(12) United States Patent
Kawamura et al.

(10) Patent No.: US 7,763,462 B2
(45) Date of Patent: Jul. 27, 2010

(54) BDNF FACILITATION OF OOCYTE, ZYGOTE AND PRE-IMPLANTATION EMBRYO MATURATION

(75) Inventors: Kazuhiro Kawamura, Akita (JP); Aaron J. W. Hsueh, Stanford, CA (US); Sabine M. Mulders, Oss (NL)

(73) Assignees: The Board of Trustees of the Leland Stanford Junior University, Palo Alto, CA (US); N.V. Organon, Oss (NL)

( * ) Notice: Subject to any disclaimer, the term of this patent is extended or adjusted under 35 U.S.C. 154(b) by 153 days.

(21) Appl. No.: 11/762,606

(22) Filed: Jun. 13, 2007

(65) Prior Publication Data

US 2007/0294780 A1    Dec. 20, 2007

Related U.S. Application Data

(60) Provisional application No. 60/814,475, filed on Jun. 16, 2006.

(51) Int. Cl.
*C12N 5/00* (2006.01)
*A61B 17/43* (2006.01)

(52) U.S. Cl. ............ 435/375; 435/384; 600/33

(58) Field of Classification Search ............ None
See application file for complete search history.

(56) References Cited

OTHER PUBLICATIONS

Takahashi et al. GnRH Antagonist improve Blastocyst Quality and Pregnancy Outcome After Multiple Failures of IVF/ICSI-ET with a GNRH Agonist Protocol, Journal Assisted Reproduc. Geneti., 2004, vol. 21, pp. 317-322.*
Da Silva et al., "Brain—derived neurotrophic factor promotes bovine oocyte cytoplasmic competence for embryo development", Reproduction, 2005, 129(4):423-434.
De La Fuente et al., "Epidermal growth factor enhances preimplantation developmental competence of maturing mouse oocytes", Hum. Reprod., 1999, 14(12):3060-3068.
Fulka et al., "Nuclear and cytoplasmic determinants involved in the regulation of mammalian oocyte maturation", Mol. Hum. Reprod., 1998, 4(1):41-49.
Ikeda et al., "Effects of midkine during in vitro maturation of bovine oocytes on subsequent developmental competence", Biol. Reprod., 2000, 63(4):1067-1074.
Kawamura et al, "Ovarian brain—derived neurotrophic factor (BDNF) promotes the development of oocytes into preimplantation embryos," Proc. Natl. Acad. Sci. USA, 2005, 102(26):9206-9211.
Kawamura et al., "Paracrine regulation of mammalian oocyte maturation and male germ cell survival", Proc. Natl. Acad. Sci. USA, 2004, 101(19):7323-7328.
Park et al., "EGF—like growth factors as mediators of LH action in the ovulatory follicle", Science, 2004, 303 (5658):682-684.
Seifer et al., "Brain—derived neurotrophic factor: a novel human ovarian follicular protein", J Clin. Endocrinol. Metabol., 2002, 87(2):655-659.
Silva and Knight, "Modulatory actions of activin-A and follistatin on the developmental competence of in vitro—matured bovine oocytes", Biol. Reprod., 1998, 58(2):558-565.
Spears et al., "The role of neurotrophin receptors in female germ-cell survival in mouse and human", Development, 2003, 130(22):5481-5491.

* cited by examiner

*Primary Examiner*—Deborah Crouch
(74) *Attorney, Agent, or Firm*—Bozicevic, Field & Francis LLP; Pamela J. Sherwood

(57) ABSTRACT

Compositions and methods are provided for enhancing the survival and promoting the maturation of mammalian oocytes, zygotes and preimplantation embryos. BDNF or BDNF agonists may be administered to an individual, or to cells in vitro, to enhance cellular maturation, embryo growth and fertilization. Accordingly, compositions comprising BDNF are herein presented for use in promoting in vivo oocyte maturation as well as for use as a component in culture media for promoting preimplantation maturation of zygotes and embryos, for instance, for use with in vitro fertilization procedures and for the production of stem cells. Additionally, compounds that interfere with the binding of BDNF to its receptor may be administered to an individual to prevent oocyte maturation, thereby acting as a contraceptive. The BNDF receptor, TrkB, and BDNF also find use in the screening and design of agonists and antagonists for use in the methods of the invention.

9 Claims, 9 Drawing Sheets

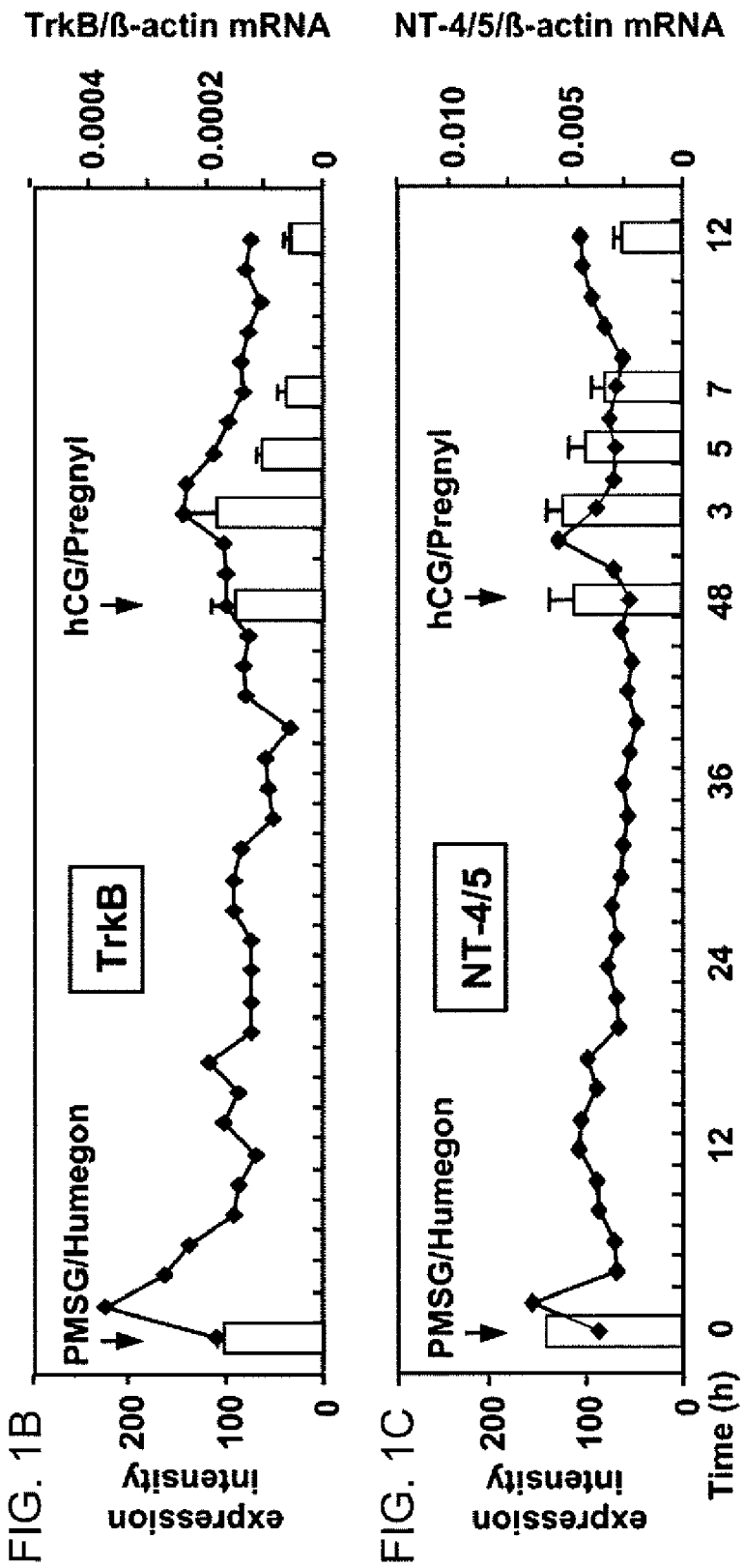

FIG. 2B
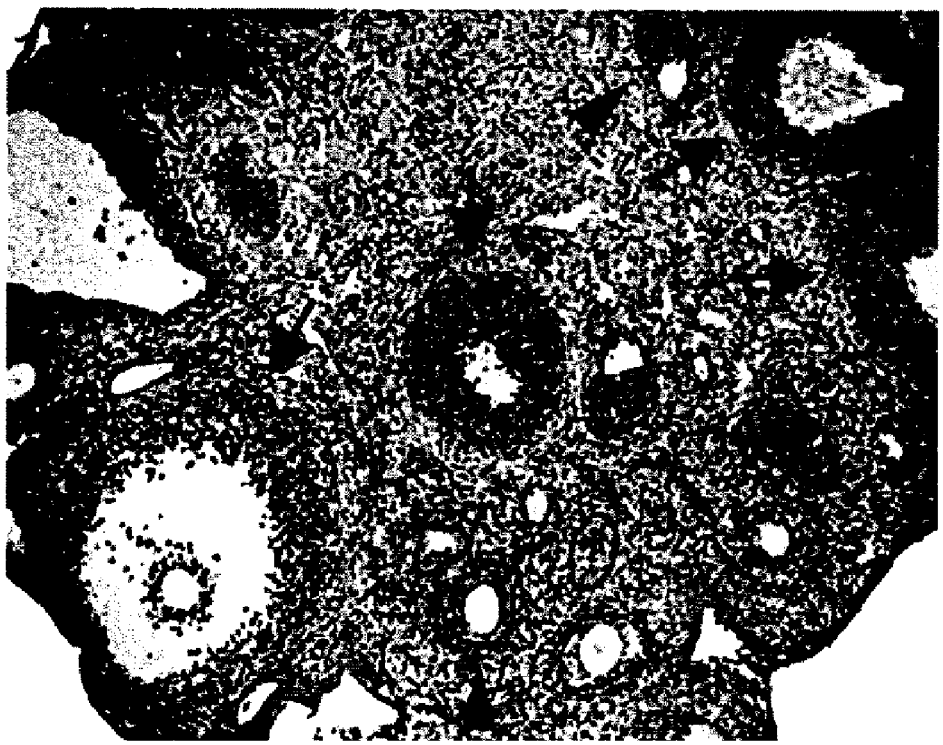
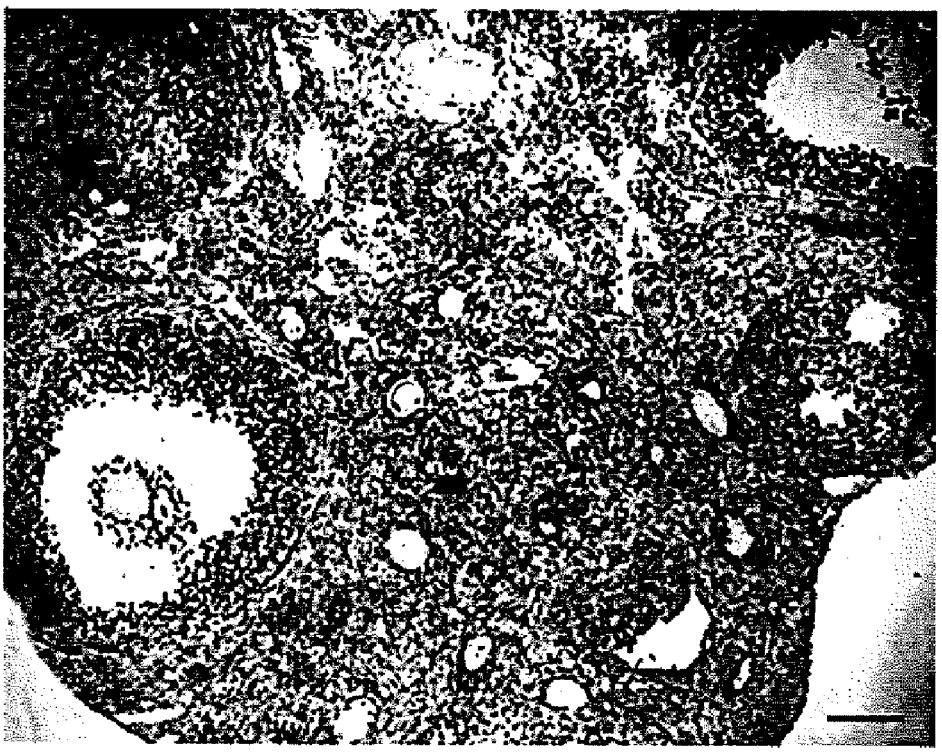

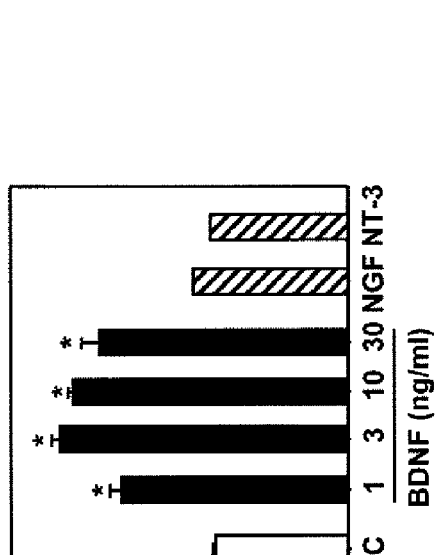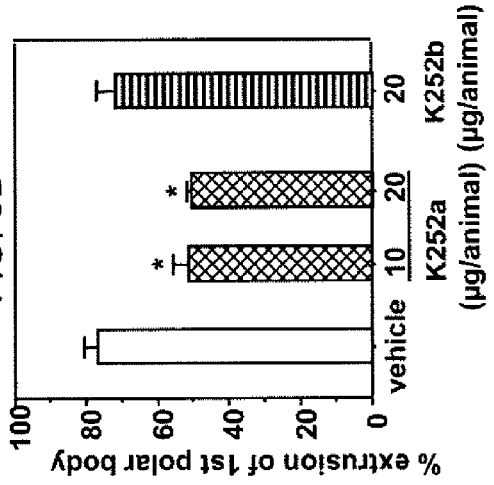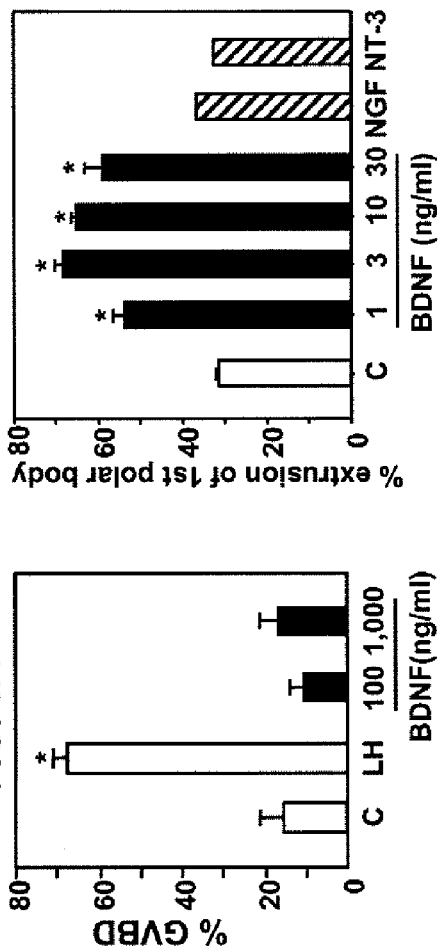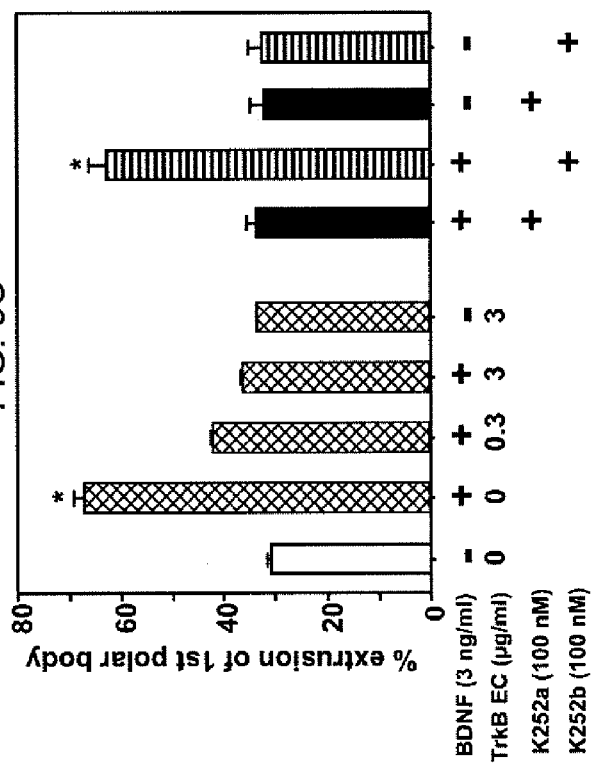

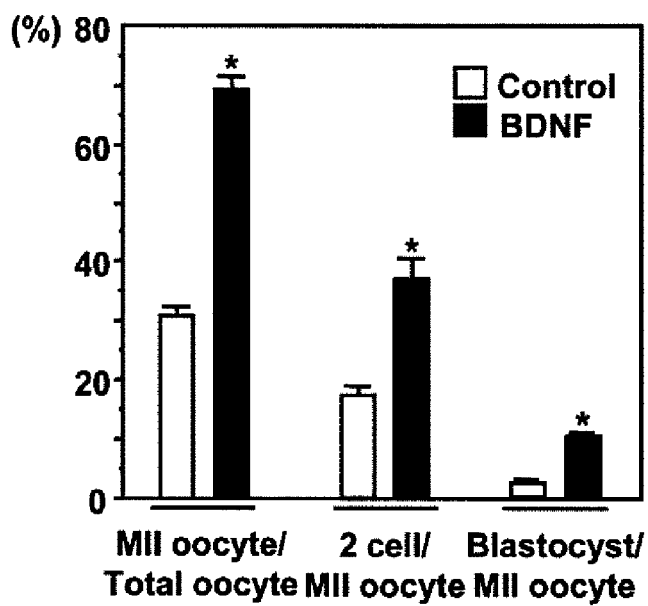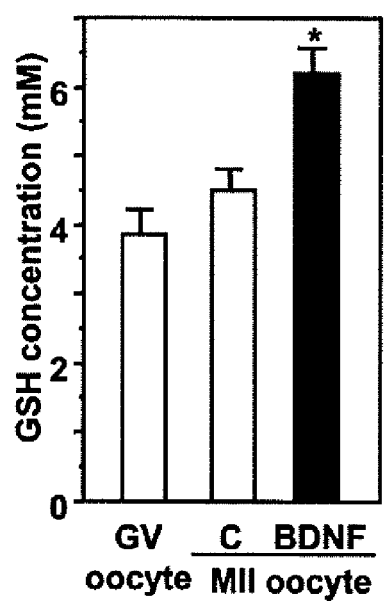
FIG. 4A
FIG. 4B

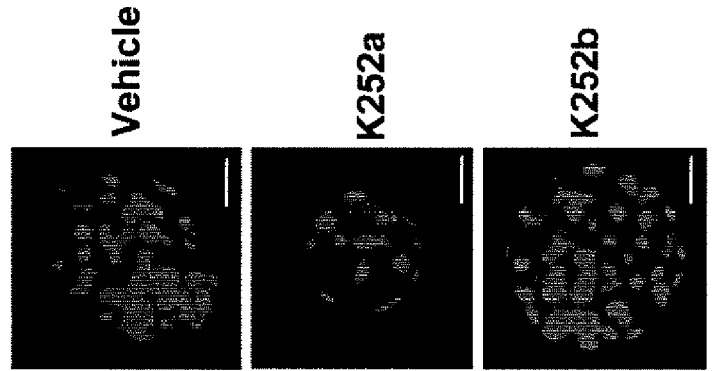
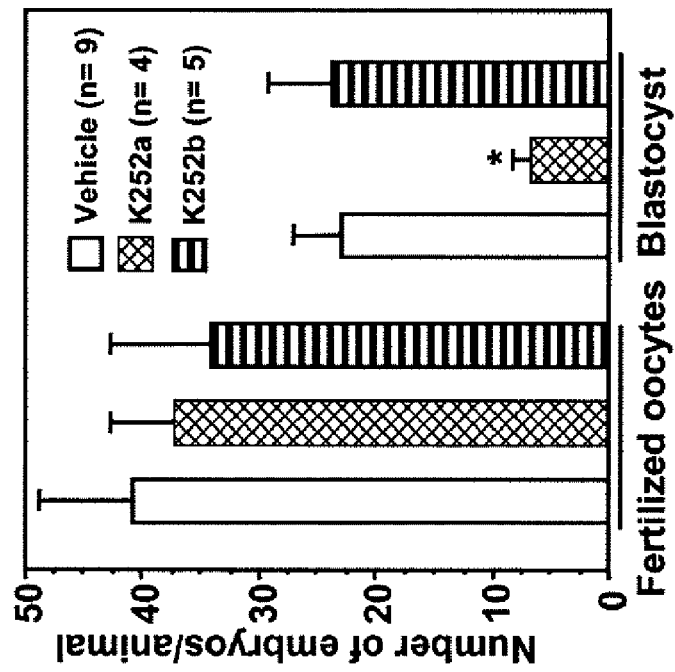

SEQUENCE LISTING

<160> NUMBER OF SEQ ID NOS: 4

<210> SEQ ID NO 1
<211> LENGTH: 918
<212> TYPE: DNA

<213> ORGANISM: human

<400> SEQUENCE: 1

```
ggtgaaagaa agccctaacc agttttctgt cttgtttctg ctttctccct acagttccac    60
caggtgagaa gagtgatgac catccttttc cttactatgg ttatttcata ctttggttgc   120
atgaaggctg cccccatgaa agaagcaaac atccgaggac aaggtggctt ggcctaccca   180
ggtgtgcgga cccatgggac tctggagagc gtgaatgggc caaggcagg ttcaagaggc    240
ttgacatcat tggctgacac tttcgaacac gtgatagaag agctgttgga tgaggaccag   300
aaagttcggc ccaatgaaga aaacaataag gacgcagact gtacacgtc cagggtgatg    360
ctcagtagtc aagtgccttt ggagcctcct cttctctttc tgctggagga atacaaaaat   420
tacctagatg ctgcaaacat gtccatgagg gtccggcgcc actctgaccc tgcccgccga   480
ggggagctga gcgtgtgtga cagtattagt gagtgggtaa cggcggcaga caaaaagact   540
gcagtggaca tgtcgggcgg gacggtcaca gtccttgaaa aggtccctgt atcaaaaggc   600
caactgaagc aatacttcta cgagaccaag tgcaatccca tgggttacac aaaagaaggc   660
tgcaggggca tagacaaaag gcattggaac tcccagtgcc gaactaccca gtcgtacgtg   720
cgggccctta ccatggatag caaaaagaga attggctggc gattcataag gatagacact   780
tcttgtgtat gtacattgac cattaaaagg ggaagatagt ggatttatgt tgtatagatt   840
agattatatt gagacaaaaa ttatctattt gtatatatac ataacagggt aaattattca   900
gttaagaaaa aaataatt                                                   918
```

<210> SEQ ID NO 2
<211> LENGTH: 255
<212> TYPE: PRT
<213> ORGANISM: human

<400> SEQUENCE: 2

```
Met Thr Ile Leu Phe Leu Thr Met Val Ile Ser Tyr Phe Gly Cys Met
  1               5                  10                  15
Lys Ala Ala Pro Met Lys Glu Ala Asn Ile Arg Gly Gln Gly Gly Leu
             20                  25                  30
Ala Tyr Pro Gly Val Arg Thr His Gly Thr Leu Glu Ser Phe Thr Val
         35                  40                  45
Asn Gly Pro Lys Ala Gly Ser Arg Gly Leu Thr Ser Leu Ala Asp Thr
     50                  55                  60
Phe Glu His Val Ile Glu Glu Leu Leu Asp Glu Asp Gln Lys Val Arg
 65                  70                  75                  80
Pro Asn Glu Glu Asn Asn Lys Asp Ala Asp Leu Tyr Thr Ser Arg Val
                 85                  90                  95
Met Leu Ser Ser Gln Val Pro Leu Glu Pro Phe Thr Pro Leu Leu Phe
            100                 105                 110
Leu Leu Glu Glu Tyr Lys Asn Tyr Leu Asp Ala Ala Asn Met Ser Met
        115                 120                 125
Arg Val Arg Arg His Ser Asp Pro Ala Arg Arg Gly Glu Leu Ser Val
    130                 135                 140
Cys Asp Ser Ile Ser Glu Trp Val Thr Ala Ala Asp Lys Lys Thr Ala
145                 150                 155                 160
Val Asp Met Ser Gly Gly Thr Phe Thr Val Thr Leu Glu Lys Val
                165                 170                 175
Pro Val Ser Lys Gly Gln Leu Lys Gln Tyr Phe Tyr Glu Thr Lys Cys
            180                 185                 190
```

```
Asn Pro Met Gly Tyr Thr Lys Glu Gly Cys Arg Gly Ile Asp Lys Arg
        195                 200                 205

His Trp Asn Ser Gln Cys Arg Thr Thr Gln Ser Tyr Val Arg Ala Leu
        210                 215                 220

Thr Met Asp Ser Phe Thr Lys Lys Arg Ile Gly Trp Arg Phe Ile Arg
225                 230                 235                 240

Ile Asp Thr Ser Cys Val Cys Thr Leu Thr Ile Lys Arg Gly Arg
                245                 250                 255

<210> SEQ ID NO 3
<211> LENGTH: 822
<212> TYPE: PRT
<213> ORGANISM: human

<400> SEQUENCE: 3

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
```

-continued

```
            305                 310                 315                 320
Gly Ala Ile Leu Asn Glu Ser Lys Tyr Ile Cys Thr Lys Ile His Val
                325                 330                 335
Thr Asn His Thr Glu Tyr His Gly Cys Leu Gln Leu Asp Asn Pro Thr
                340                 345                 350
His Met Asn Asn Gly Asp Tyr Thr Leu Ile Ala Lys Asn Glu Tyr Gly
                355                 360                 365
Lys Asp Glu Lys Gln Ile Ser Ala His Phe Met Gly Trp Pro Gly Ile
                370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
                405                 410                 415
Ile Pro Ser Thr Asp Val Thr Asp Lys Thr Gly Arg Glu His Leu Ser
                420                 425                 430
Val Tyr Ala Val Val Ile Ala Ser Val Val Gly Phe Cys Leu Leu
                435                 440                 445
Val Met Leu Phe Leu Leu Lys Leu Ala Arg His Ser Lys Phe Gly Met
                450                 455                 460
Lys Gly Pro Ala Ser Val Ile Ser Asn Asp Asp Ser Ala Ser Pro
465                 470                 475                 480
Leu His His Ile Ser Asn Gly Ser Asn Thr Pro Ser Ser Ser Glu Gly
                485                 490                 495
Gly Pro Asp Ala Val Ile Ile Gly Met Thr Lys Ile Pro Val Ile Glu
                500                 505                 510
Asn Pro Gln Tyr Phe Gly Ile Thr Asn Ser Gln Leu Lys Pro Asp Thr
                515                 520                 525
Phe Val Gln His Ile Lys Arg His Asn Ile Val Leu Lys Arg Glu Leu
                530                 535                 540
Gly Glu Gly Ala Phe Gly Lys Val Phe Leu Ala Glu Cys Tyr Asn Leu
545                 550                 555                 560
Cys Pro Glu Gln Asp Lys Ile Leu Val Ala Val Lys Thr Leu Lys Asp
                565                 570                 575
Ala Ser Asp Asn Ala Arg Lys Asp Phe His Arg Glu Ala Glu Leu Leu
                580                 585                 590
Thr Asn Leu Gln His Glu His Ile Val Lys Phe Tyr Gly Val Cys Val
                595                 600                 605
Glu Gly Asp Pro Leu Ile Met Val Phe Glu Tyr Met Lys His Gly Asp
                610                 615                 620
Leu Asn Lys Phe Leu Arg Ala His Gly Pro Asp Ala Val Leu Met Ala
625                 630                 635                 640
Glu Gly Asn Pro Pro Thr Glu Leu Thr Gln Ser Gln Met Leu His Ile
                645                 650                 655
Ala Gln Gln Ile Ala Ala Gly Met Val Tyr Leu Ala Ser Gln His Phe
                660                 665                 670
Val His Arg Asp Leu Ala Thr Arg Asn Cys Leu Val Gly Glu Asn Leu
                675                 680                 685
Leu Val Lys Ile Gly Asp Phe Gly Met Ser Arg Asp Val Tyr Ser Thr
                690                 695                 700
Asp Tyr Tyr Arg Val Gly Gly His Thr Met Leu Pro Ile Arg Trp Met
705                 710                 715                 720
Pro Pro Glu Ser Ile Met Tyr Arg Lys Phe Thr Thr Glu Ser Asp Val
                725                 730                 735
```

```
Trp Ser Leu Gly Val Val Leu Trp Glu Ile Phe Thr Tyr Gly Lys Gln
        740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu
        770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820

<210> SEQ ID NO 4
<211> LENGTH: 2610
<212> TYPE: DNA
<213> ORGANISM: human

<400> SEQUENCE: 4
gagttaagag agccgcaagc gcagggaagg cctccccgca cgggtggggg aaagcggccg     60
gtgcagcgcg gggacaggca ctcgggctgg cactggctgc tagggatgtc gtcctggata    120
aggtggcatg gacccgccat ggcgcggctc tggggcttct gctggctggt tgtgggcttc    180
tggagggccg ctttcgcctg tcccacgtcc tgcaaatgca gtgcctctcg gatctggtgc    240
agcgaccctt ctcctggcat cgtggcattt ccgagattgg agcctaacag tgtagatcct    300
gagaacatca ccgaaatttt catcgcaaac agaaaaggt tagaaatcat caacgaagat    360
gatgttgaag cttatgtggg actgagaaat ctgacaattg tggattctgg attaaaattt    420
gtggctcata aagcatttct gaaaacagca aacctgcagc acatcaattt acccgaaaac    480
aaactgacga gtttgtctag aaacattc cgtgtcacct tg acttgtctga actgatcctg    540
gtgggcaatc catttacatg ctcctgtgac attatgtgga tcaagactct ccaagaggct    600
aaatccagtc cagacactca ggatttgtac tgcctgaatg aaagcagcaa gaatattccc    660
ctggcaaacc tgcagatacc caattgtggt ttgccatctg caaatctggc cgcacctaac    720
ctcactgtgg aggaaggaaa gtctatcaca ttatcctgta gtgtggcagg tgatccggtt    780
cctaatatgt attgggatgt tggtaacctg gtttccaaac atatgaatga aacaagccac    840
acacagggct ccttaaggat aactaacatt tcatccgatg acagtgggaa gcagatctct    900
tgtgtggcgg aaaatcttgt aggagaagat caagattctg tcaacctcac tgtgcatttt    960
gcaccaacta tcacatttct cgaatctcca acctcagacc accactggtg cattccattc   1020
actgtgaaag gcaaccccaa accagcgctt cagtggttct ataacgggg aatattgaat   1080 gagtccaaat acatctgtac taaaatacat gttaccaatc acacggagta ccacggctgc   1140
ctccagctgg ataatcccac tcacatgaac aatgggggact acactctaat agccaagaat   1200
gagtatggga aggatgagaa acagatttct gctcacttca tgggctggcc tggaattgac   1260
gatggtgcaa acccaaatta tcctgatgta atttatgaag attatggaac tgcagcgaat   1320
gacatcgggg acaccacgaa cagaagtaat gaaatcccctt ccacagacgt cactgataaa   1380
accggtcggg aacatctctc ggtctatgct gtggtggtga ttcgtctgtg gtgggatttt   1440
tgccttttgg taatgctgtt tctgcttaag ttggcaagac actccaagtt tggcatgaaa   1500
ggcccagcct ccgttatcag caatgatgat gactctgcca gcccactcca tcacatctcc   1560
```

```
aatgggagta acactccatc ttcttcggaa ggtggcccag atgctgtcat tattggaatg    1620
accaagatcc ctgtcattga aaatccccag tactttggca tcaccaacag tcagctcaag    1680
ccagacacat ttgttcagca catcaagcga cataacattg ttctgaaaag ggagctaggc    1740
gaaggagcct ttggaaaagt gttcctagct gaatgctata acctctgtcc tgagcaggac    1800
aagatcttgg tggcagtgaa gaccctgaag gatgccagtg acaatgcacg caaggacttc    1860
caccgtgagg ccgagctcct gaccaacctc cagcatgagc acatcgtcaa gttctatggc    1920
gtctgcgtgg agggcgaccc cctcatcatg gtctttgagt acatgaagca tggggacctc    1980
aacaagttcc tcagggcaca cggccctgat gccgtgctga tggctgaggg caacccgccc    2040
acggaactga cgcagtcgca gatgctgcat atagcccagc agatcgccgc gggcatggtc    2100
tacctggcgt cccagcactt cgtgcaccgc gatttggcca ccaggaactg cctggtcggg    2160
gagaacttgc tggtgaaaat cggggacttt gggatgtccc gggacgtgta cagcactgac    2220
tactacaggg tcggtggcca cacaatgctg cccattcgct ggatgcctcc agagagcatc    2280
atgtacagga aattcacgac ggaaagcgac gtctggagcc tgggggtcgt gttgtgggag    2340
attttcacct atggcaaaca gccctggtac cagctgtcaa acaatgaggt gatagagtgt    2400
atcactcagg gccgagtcct gcagcgaccc cgcacgtgcc cccaggaggt gtatgagctg    2460
atgctggggt gctggcagcg agagccccac atgaggaaga acatcaaggg catccatacc    2520
ctccttcaga acttggccaa ggcatctccg gtctacctgg acattctagg ctagggccct    2580 tttcccccaga ccgatccttc ccaacgtact                                     2610
```

US 7,763,462 B2

BDNF FACILITATION OF OOCYTE, ZYGOTE AND PRE-IMPLANTATION EMBRYO MATURATION

CROSS-REFERENCE TO RELATED APPLICATIONS

This applications claims benefit of priority to U.S. provisional application 60/814,475, filed Jun. 16, 2006, which is herein incorporated by reference.

FEDERALLY-SPONSORED RESEARCH OR DEVELOPMENT

This invention was made with Government support under contract HG000205 awarded by the National Institutes of Health. The Government has certain rights in this invention.

BACKGROUND OF THE INVENTION

The majority of oocytes within the adult female ovary are enveloped and surrounded by follicular somatic cells (such as granulosa, theca and cumulus cells). During the early stages of development, the surrounded oocytes are maintained in a prolonged stage of first meiotic prophase. The growth and maturation of mammalian follicle cells and oocytes are dependent upon and intricately controlled by hormones, including gonadotropins, such as follicle stimulating hormone (FSH) and luteinizing hormone (LH) secreted by the anterior pituitary, and other local paracrine factors secreted by the surrounding follicular somatic cells.

Periodically, a group of primordial follicles enters a stage of follicular growth. During this time, the oocyte undergoes a large increase in volume and the number of surrounding follicular granulosa cells increases. In early stages of the cycle, maturing follicles respond to FSH with further growth and cellular proliferation. In later stages, FSH induces the formation of LH receptors on the granulosa cells. In response to LH, the first oocyte meiotic block is removed and the granulosa and theca cells of the ovaries begin to produce EGF-like factors and insulin-like 3. In response to these factors, the nuclear membranes of competent oocytes are then broken down (germinal vesicle nuclear envelope breakdown), the chromosomes assemble to undergo the first meiotic division and the first polar body is extruded in preparation of the oocyte for fertilization.

Because LH acts exclusively on somatic cells in the ovaries (e.g., granulosa and theca cells), local paracrine factors are involved in the regulation of oocyte meiosis arrest and optimal oocyte maturation. Therefore, in addition to the pituitary hormones FSH and LH, other factors are involved in the maturation process. For instance, the maturing oocyte synthesizes paracrine factors that allow the follicle cells to proliferate; while the follicle cells secrete growth and differentiation factors (for example TGF-$\beta$2, VEGF, EGF, leptin, and FGF2) that enhance angiogenesis and allow the oocyte to grow and mature. Another factor secreted by follicular somatic cells is brain-derived nuerotrophic factor (BDNF).

Because of the importance of oocyte maturation and pre-implantation embryo development, there is a strong interest in developing novel compositions that are clinically useful for enhancing oocyte maturation and promoting pre-implantation embryo growth. Accordingly, the present invention is of great clinical interest because it provides novel BDNF containing compositions that are useful for the modulation of oocyte, zygote and preimplantation embryo development.

SUMMARY OF THE INVENTION

Compositions and methods are provided for promoting the maturation and enhancing the survival of oocytes, zygotes and embryonic cells by administration of brain derived neurotrophic factor (BDNF). BDNF is shown to function in the development and maturation of follicles and oocytes. BDNF interacts with its receptor, TrkB, which is expressed in oocytes, and thereby functions to enhance oocyte growth and maturation. Accordingly, in vivo and in vitro treatment with BDNF promotes oocyte and embryo development and maturation.

In one embodiment of the invention, BDNF or BDNF agonists are administered to an individual, or to cells in vitro, to enhance oocyte maturation, and may further promote subsequent zygote and pre-implantation embryo development. In certain embodiments, the methods of the invention are useful for in vivo oocyte maturation enhancement. After the mid-cycle LH surge that induces the rupture of the preovulatory follicle, a released oocyte may not be adequately matured and will therefore have a reduced capacity for fertilization and further development into an embryo. The in vivo administration of BDNF functions to increase the development of the oocyte both pre and post-ovulatory follicle rupture. In such methods, BDNF may be administered for an extended period of time during a female's ovulatory cycle, e.g., one week or more.

In certain embodiments, the methods of the invention are useful for enhancing in vitro oocyte, zygote and pre-implantation embryo development. In such methods, BDNF is included as a component in a tissue culture media, or is otherwise contacted with an oocyte, zygote or pre-implantation embryo for use in conjunction with in vitro fertilization procedures, in vitro embryonic stem cell production, and the like. Derivation of embryonic stem cells may include parthenogenetic activation, and nuclear transfer, e.g. from somatic cells.

In some embodiments, compounds that interfere with the binding of BDNF to its receptor, TrkB, are administered to an individual to prevent oocyte maturation, thereby acting as a contraceptive. TrkB and BDNF are useful separately or in combination in the screening and design of agonists and antagonists for use in the methods of the invention.

BRIEF DESCRIPTION OF THE FIGURES

FIGS. 1A-1D. FIGS. 1A-1C are line graphs representing DNA microarray data depicting the expression intensity of the indicated transcripts (on the left y axis). The values for the expression intensity were derived from the integration of hybridization signals from multiple probe sets for individual genes. FIG. 1A Indicates gonadotropin regulation of BDNF transcript expression. Specifically, hCG stimulation of BDNF proteins in mouse ovaries is shown. FIG. 1B Indicates gonadotropin regulation of the BDNF receptor TrkB. Specifically, hCG stimulation of TrkB proteins in mouse ovaries are shown. FIG. 1C Indicates gonadotropin regulation of NT-4/5. Specifically, hCG stimulation of NT-4/5 proteins in mouse ovaries are shown. FIG. 1D is a bar graph depicting quantitative real time results (right y axis) for gonadotropin stimulation of BDNF expression. Ovarian content of BDNF ($\mu$g/mg ovarian wet weight) was measured by ELISA (mean±SEM, n=3), P<0.05 vs. 0 h of PMSG treatment.

FIGS. 2A-2C depict the localization of BDNF, TrkB, and p75 NTR transcripts as well as BDNF and TrkB antigens in the mouse ovary. FIG. 1A depicts the expression of BDNF, TrkB, and p75 NTR mRNAs in isolated ovarian cells obtained from mice 48 h after PMSG treatment was detected by using nested RT-PCR. Levels of β-actin serve as loading controls. Total ovarian cDNA was used in positive control tests, whereas no template DNA was included for negative controls. Ov=ovary; C=negative control; Oo=oocyte; MGC=mural granulose cells; and CC=cumulus cells. FIG. 1B depicts immunohistochemical detection of BDNF in ovaries of PMSG-primed mice 7 h after hCG injection. BDNF was found in cumulus and mural granulose cells of preovulatory follicles (arrows), whereas weaker staining was found in mural granulose cells of small antral follicles (arrowheads). The upper slide shows BDNF staining and the lower slide shows a negative control. (Scale bars, 40 μm.) FIG. 1C depicts the immunofluorescence staining of TrkB in an oocyte at the metaphase I stage. The upper slides show TrkB staining, while the lower slides show a negative control. The overlay pictures show the combined staining of plasma membrane-bound TrkB and nuclear DNA (Hoechst staining).

FIGS. 3A-3D depict BDNF stimulation of first polar body extrusion by cultured oocytes. FIG. 3A indicates the lack of effect of BDNF on GVBD of oocytes. Preovulatory follicles were cultured without (control, C) or with 5 μg/ml LH or BDNF for 6 h before evaluation of oocytes undergoing GVBD (n=3, 39-68 oocytes per experiment). FIG. 3B indicates the effects of BDNF treatment on first polar body extrusion by oocytes in vitro. COCs from preovulatory follicles were cultured without (controls C) or with BDNF for 20 h. Some COCs were treated with 10 ng/ml NGF or 10 ng/ml NT-3. After culture, the percentage of oocytes showing first polar body extrusion was determined (n=3, 30-148 oocytes per experiment). FIG. 3C indicates the antagonistic effects of the TrkB ectodomain (TrkB EC) and the Trk receptor inhibitor K252a on BDNF stimulation of first polar body extrusion. COCs were cultured with BDNF with or without TrkB ectodomain, K252a, or K252b (n=3, 11-82 oocytes per experiment). FIG. 3C indicates the effect of the Trk receptor inhibitor on the extrusion of first polar body of oocytes in vivo. PMSG-primed mice were treated with hCG with or without K252a or the related K252b (i.p.). After 12 h of treatment, the percentage of ovulated oocytes showing first polar body extrusion was evaluated (n=4).*, P<0.05 vs. control or vehicle group.

FIGS. 4A-E depict BDNF conditioning of oocytes for development into preimplantation embryos. FIG. 4A is a bar graph indicating the percentage of MII oocytes that developed to two-cell or blastocyst-stage embryos. Specifically, COCs obtained from preovulatory follicles were cultured without (control) or with BDNF (3 ng/ml) for 16 h. After progression to the MII stage, oocytes were inseminated and cultured for 5 days more without hormones. The percentage of MII oocytes that developed to two-cell or blastocyst-stage embryos were evaluated (n=5, 34-95 oocytes per experiment). FIG. 4B indicates the effects of BDNF treatment on glutathione (GSH) content in oocytes. After treatment of COCs for 16 h without (control, C) or with BDNF, glutathione levels in oocytes at MII oocytes were evaluated (mean±SEM, n=6). FIG. 4C depicts the effects of K252a treatment in vivo on the progression of zygotes into blastocysts in vitro. PMSG-primed mice were treated with hCG with or without K252a or K252b (10 μg, injections at 0, 4, and 8 h after hCG). After initial injection, mice were allowed to mate with fertile males. Fertilized oocytes were cultured for 5 days, and the number of blastocyst embryos was evaluated. FIG. 4D depicts the effects of K252a treatment on the number of cells in the blastocysts. FIG. 4E depicts the epifluorescence images of blastocysts stained with Hoechst 33342. (Scale bar, 20 μm.)*, P<0.05 vs. control or vehicle group.

DESCRIPTION OF THE SPECIFIC EMBODIMENTS

Figure 1A:
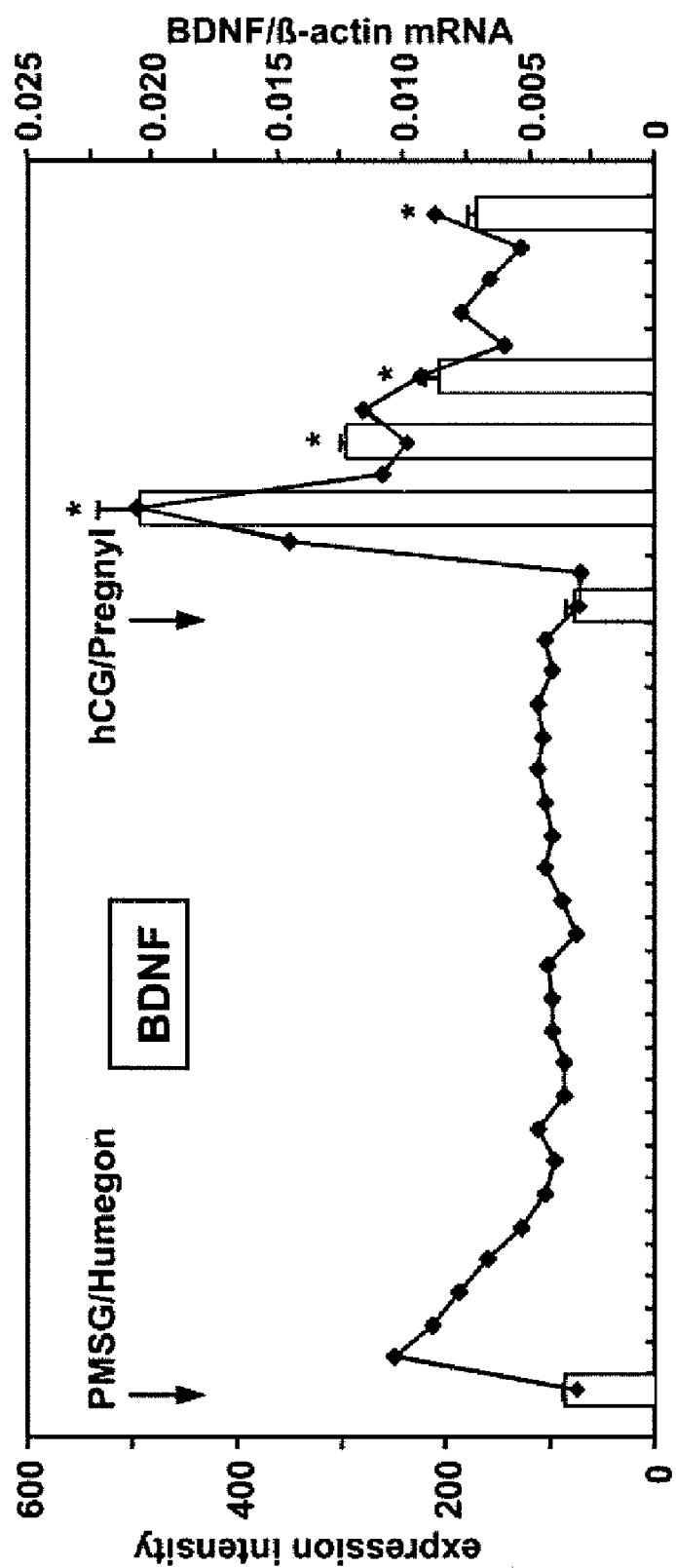

Compositions and methods are provided for enhancing the survival and promoting the maturation of mammalian oocytes, zygotes and preimplantation embryos. By contacting a mammalian oocyte, zygote or preimplantation embryo with BDNF, oocyte cellular competence is increased and preimplantation embryo development enhanced. In view of this, BDNF or BDNF agonists are administered to an individual, or to cells in vitro, to enhance cellular maturation, fertilization and embryo growth. Compositions having BDNF activity BDNF are useful in promoting in vivo oocyte maturation. Such composition are also useful as a component in culture media for promoting preimplantation maturation of zygotes and embryos, for instance, for use with in vitro fertilization procedures and for the production of embryonic stem cells. Further, compounds that interfere with the binding of BDNF to its receptor may be administered to an individual to prevent oocyte maturation, thereby acting as a contraceptive. The BNDF receptor, TrkB, and BDNF also find use in the screening and design of agonists and antagonists for use in the methods of the invention. Additionally, BDNF may also be used alone or in combination with other factors (for instance, with EGF) as a component in culture media to promote oocyte maturation in the development of mammalian embryonic stem cells, e.g., following somatic cell nuclear transfer, parthenogenetic activation, etc.

The compositions and methods of the invention find use in a wide variety of animal species, particularly including mammalian species. Animal models, particularly small mammals, e.g. murine, lagomorpha, etc. are of interest for experimental investigations. Other animal species may benefit from improvements in in vitro fertilization, e.g. horses, cattle, rare zoo animals, such as but not limited to: panda bears, large cats, etc. Humans are of particular interest for both enhancing oocyte maturation, improving both in vivo and in vitro fertilization and for methods of contraception. The compositions and methods of the invention also find use in the generation of in vitro cultured mammalian embryonic stem cells.

Before the subject invention is further described, it is to be understood that the invention is not limited to the particular embodiments of the compositions and methods described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Oocyte and Oocyte Maturation.

The meiotic division of mammalian oocytes begins with one primary germ cell (oocyte), which gives rise to only one mature ovum (egg). In normal mammalian development, oocytes become developmentally arrested in the ovaries at the germinal vesicle stage in prophase of the first meiotic division (G2/M transition). In response to the mid-cycle LH surge, oocytes of preovulatory follicles resume meiosis. The first meiotic division is completed with the extrusion of a diploid set of chromosomes into the first polar body while another diploid set of chromosomes remain within the cytoplasm of the oocyte. The cells then proceed to the second meiotic division, where the oocyte becomes arrested at metaphase ("Met II"). Met II oocytes are mature, and can be ovulated and fertilized.

Meiotic arrest of the oocyte is most likely maintained by follicular purines that increase cAMP levels in the oocyte. A decrease in intra-oocyte CAMP levels is required for meiotic resumption in oocytes. The effect of LH on cells of the ovaries is to stimulate the production and release of EGF-like factors, from granulosa cells, insulin-like 3, from theca cells, and BDNF from other ovarian somatic cells. The effect of EGF-like factors and insulin-like 3 on oocytes is the initiation of germinal vesicle (nuclear envelope) breakdown. The effect of BDNF on oocytes is the promotion of the extrusion of the first polar body. Accordingly, BDNF is shown herein to be important in oocyte maturation and is significant for the completion of the first meiotic division and the resumption of meiosis. For instance, BDNF promotes further cytoplasmic changes that are essential for monospermic fertilization, processing of the sperm, and for pre-implantation embryo development. Additionally, the evidence provided herein demonstrates that follicle rupture (via somatic cell interactions) and oocyte maturation (germ cells) can be separated, providing a basis for contraception through blocking the interaction between BDNF and its receptor, TrkB, expressed exclusively in the oocyte.

BDNF

BDNF belongs to the neurotrophin hormone family, which group also includes nerve growth factor (NGF), neurotrophin-3 (NTF3), and neurotrophin-4/5 (NTF5). These four genes encode pre-pro-neurotrophins. With the exception of NT4/5, neurotrophin sequences are highly conserved in mammals. The processed proteins have a size of ~13,000 D, and they exist in solution as noncovalently linked homodimers (for review, see Barde, Y.-A. 1990. The nerve growth factor family. Prog. Growth Factor Res. 2: 237-348; and Ibáñez, C. F. 1998. Emerging themes in structural biology of neurotrophic factors. Trends Neurosci. 21: 438-444). The mature form of each neurotrophin are about 120 residues, approximately 48% of which are identical among all three neurotrophins, which includes six cysteine residues that have been shown to form three intrachain disulfide bridges (e.g., NGF).

BDNF is a nuerotrophic factor typically found in the neurons of the central nervous system (CNS). BDNF is known to function to control neurogenesis by helping to support the survival and growth of neurons. It is primarily active in the hippocampus, cortex, and basal forebrain. Exposure to corticosterone decreases the expression of BDNF. NGF, BDNF and NT-3 all have at least two forms of primary precursors with at least two translational start sites. BDNF has a short form precursor (about 1.6 kb) and a long form precursor (about 4 kb). The short form precursor is encoded on a single exon whereas the long form precursor is encoded on at least two exons. For convenience, the gene, coding sequences, and amino acid sequence of BDNF are provided in SEQ ID NO:1 and SEQ ID NO:2. From the cDNA sequence, it has been deduced that the BDNF protein is synthesized as about a 187 amino-acid (aa) preproprotein and the mature form of the protein contains about 119 aa.

Mimetics and agonists of BDNF are known in the art. For example, peptide mimetics are described by O'Leary and Hughes (2003) J. Biol. Chem. 278(28):25738-44. Small, dimeric peptides were designed to mimic a pair of solvent-exposed loops important for the binding and activation of the BDNF receptor, trkB. The monomer components that make up the dimers are based on a monocyclic monomeric peptide mimic of a single loop of BDNF (loop 2). Also known are BDNF antagonists. For example, as described by Debeir et al. (1999) PNAS 96:4067-4072, a small peptide, C(92-96), blocks NGF-TrkA interactions.

TrkB and p75.

Neurotrophins, such as BDNF, bind to two different classes of transmembrane receptor proteins, Trks (tropomyosin receptor kinases) and the neurotrophin receptor p75. Because neurotrophins can bind to two different receptors a dual system has evolved that allows the transduction of very different signals following ligand binding, for instance, activation of the Trk receptors can enhance cell survival while activation of p75 can initiate cell death. These two classes of receptors also directly interact thereby allowing fine tuning and cross talk of their signaling cascades.

The Trk receptors belong to the tyrosine kinase family of receptors. The intracellular tyrosine kinase domains are highly related (~80% amino acid identity), however, the extracellular ligand binding domains are somewhat divergent (~30%). Three Trk receptor genes have been identified in mammals, these include: TrkA (first identified as an NGF receptor), TrkB and TrkC. Nerve growth factor (NGF) is the preferred ligand for TrkA, BDNF and NT4/5 are preferred for TrkB, and NT3 for TrkC; however, these preferences are not absolute, for instance, NT3 is also a ligand for TrkA and TrkB. For convenience, the nucleic acid sequences of the TrkB receptor is provided as SEQ ID NO: 3. The TrkB nucleic acid sequence is set forth herein as SEQ ID NO:4.

Known inhibitors of Trk receptors include the molecule K-252a, and derivatives thereof, for example as described by U.S. Pat. No. 5,468,872; and International Application WO/9507911, herein incorporated by reference. The Trk receptors are tyrosine kinases, and as such may be inhibited by inhibitors of this class of enzyme, or by molecules that compete for the binding site of ligands, e.g. BDNF.

Inhibitor and agonists also include, for example, antibodies and fragments thereof that bind to and block or activate the Trk B receptor.

Methods of Enhancing Fertility

BDNF, BDNF agonists and mimetics, analogs and variants thereof, and agents that bind to Trk B and are capable of activating the Trk B receptor, are useful for promoting oocyte maturation and development and are therefore useful for enhancing fertility. Accordingly, BDNF and BDNF agonists are useful for increasing fertility in vivo, as well as in in vitro culture methods for increasing fertility, e.g., in combination with in vitro fertilization protocols and techniques.

For in vivo usage, the dose to be delivered will vary and is dependent on the particular procedures to be used and the route of administration but will be effective to permit oocytes to pass to maturation, i.e., to proceed to the second meiotic division, and arrest at metaphase ("Met II"), which oocytes can then be ovulated and fertilized.

For in vitro fertilization purposes BDNF and/or its agonist may be administered to an ova donor prior to or along with the administration of other factors that are useful for promoting oocyte maturation prior to or immediately after ovulation as well as included in the various culture media used in the in vitro fertilization process.

Generally, in vitro fertilization is a fertilization technique whereby an ovum is fertilized outside of a female's body. The process typically involves one or more of: hormonally controlling the ovulatory process of the donor female so as to promote and time ovulation, removing the ova from the ovaries and contacting the collected ova with viable sperm in a medium (e.g., a fluid medium) in a manner sufficient to cause fertilization. Once fertilized the resultant viable zygote may then be transferred into the uterus in a manner sufficient to establish pregnancy.

More specifically, the first step in an in vitro fertilization process typically includes treating the donor female with a regimen of fertility medications so as to stimulate the development and maturation of multiple follicles of the ovaries. Treatment may begin at any time after the beginning of the menstruation cycle, but typically begins on the third day after the onset of menstruation. The treatment usually involves the administration (e.g., injection) of at least gonadotropins, for instance, FSH and/or its analogs. Accordingly, in certain embodiments, BDNF is administered alone or in combination with one or more gonadotropins, for instance, FSH and/or its analogs, for the pretreatment of a donor female prior to collection of the ova (e.g., before and/or after ovulation). In certain embodiments, a composition containing BDNF, by itself or in combination, for instance, with a gonadotropin, is useful for administration (e.g., in oral dosage form) for in vitro fertilization procedures for the stimulation of development and maturation of ova in the follicles prior to and after ovulation.

The treatment of the donor female in preparation for ovulation should be closely monitored in order to control estradiol levels and to track follicular growth. Preovulatory treatment is typically continued for approximately 10 days or as necessary. Endogenous ovulation may be blocked and therefore controlled by use of GnRH antagonist. However, when follicular maturation is judged to be adequate, chorionic gonadotropin (e.g., β-hCG) may be administered (e.g., via injection) to induce ovulation. CG (e.g., hCG) acts as an analogue of luteinizing hormone and causes ovulation approximately 42 hours after administration. Accordingly, in certain embodiments, BDNF is administered prior to and/or along with the administration of CG to promote oocyte maturation in conjunction with the promotion of ovulation. Alternatively, BDNF can be delivered as an alternative to (e.g., as a replacement for) the delivery of CG, thereby avoiding ovarian hyper-stimulation that can result from the administration of CG.

Once one or more ovum has been ovulated the ovum may be retrieved, for instance, by use of a transvaginal technique involving ultrasound-guided needle piercing of the vaginal wall, so as to access the ovaries, and aspiration, so as to collect the ovum (ova). The follicles, ova and follicular fluids may be aspirated and then processed. After aspiration, a suitable ovum (or ova) is identified, isolated and prepared for fertilization. Prior to contact with a viable sperm sample the isolated oocyte may be preserved in a media (for instance, a fluid or culture media) containing BDNF to further enhance oocyte maturation prior to fertilization. In general, the one or more oocytes collected is typically an immature oocyte (e.g., a prophase I oocyte) which is cultured in a maturation medium containing BDNF prior to contact with sperm. Suitable maturation media include BDNF which has been combined with one or more of: HEPES buffered hamster embryo culture medium (HECM), tissue culture medium (TCM), fetal calf serum, or the like. The media may further include FSH, LH, estradiol, EGF, or the like. See Seshagine et al., Biol. Reprod., 40, 544-606, 1989; incorporated in its entirety by reference herein. The oocyte is matured until it attains the metaphase II stage (e.g., about 10 to about 40 hours post aspiration from ovarian follicles). Alternatively, metaphase II oocytes may be collected from the donor female, which may or may not be further matured in a fluid media containing BDNF. Once suitably matured the sperm is then contacted with the ovum (at a ratio of about 75,000:1) in the fluid media (e.g., fluid media containing BDNF).

The sperm may be contacted with the ovum in any manner sufficient to promote fertilization, for instance, the sperm may be pipeted onto the ovum, injected into the ovum (e.g., via intracytoplasmic sperm injection), or otherwise added to the fluid media and contacted with the ovum. Accordingly, in certain embodiments, BDNF is added to the preservation media prior to or after addition of the sperm, so as to promote both oocyte maturation and preimplantation embryo development. Fertilization may be determined by observation of two pronuclei within the cell.

After fertilization has taken place (typically about 18 hours after incubation of the ovum with the sperm) the fertilized cell (e.g., a zygote) is then passed to another specialized growth media (for instance, a media containing follicular cells), which media, in certain embodiments, also includes BDNF. In this manner BDNF may be added in addition to or as a replacement for follicular cells, which would otherwise produce BDNF. The zygote cell is then incubated in the BDNF containing growth medium until the fertilized cell has reached the 6 to 8 cell stage (e.g., has become an embryo). The time frame required for the zygote to mature to the 6 to 8 cell stage will vary but is typically between one to three days (e.g., about 48 hours). At this point the (e.g., at about 3 days) the embryo may be transferred (e.g., implanted) into a recipients uterus, for instance, via a thin, plastic catheter, which passes through the vagina and cervix.

Alternatively, if desired, an embryo at the 6 to 8 cell stage may be transferred to an extended growth BDNF containing culture medium for further development prior to implantation. The embryo may be cultured until deemed suitable for implantation. Typically, if cultured in this manner, the embryo is implanted once it has reached the blastocyst stage of development. Prior to and after implantation into a recipient, progesterone is typically administered to the recipient so as to prepare and sustain the uterus lining for implantation.

Although the above description was set forth with respect to several steps involved in the in vitro fertilization process it is to be understood that the order of the steps and/or the manner in which they are performed may vary dependent upon the specific protocol used. Accordingly, the order and nature of the steps detailed herein may vary without departing from the nature of the invention. For instance, more than one ovum may be collected, contacted with sperm in a BDNF containing media, and implanted into a suitable recipient.

Contraceptive Methods

The specificity of BDNF expression, and its role in maturation of oocytes, makes it a useful target for contraceptive design. Agents that interfere with the biological activity of BDNF can prevent oocyte maturation, potentially without affecting follicle rupture and the normal menstrual cycle. BDNF inhibitors of interest for these purposes include agents that bind to BDNF and prevent it from acting in its biological role, agents that bind to the BDNF receptor, TrkB (which agents may act as competitive inhibitors of BDNF) and agents that otherwise act as a BDNF inhibitor or antagonist. Competitive binding antagonists, for example, a polypeptide that mimics BDNF binding, without consequent receptor activation, may be used to inhibit activity. Other inhibitors are identified by screening for biological activity, e.g., in a binding assay based on the receptor ligand interaction, binding to the BDNF ligand, inhibition of the TrkB receptor; and the like.

BDNF inhibitors may be administered locally or systemically to female individuals for contraceptive purposes, in a dose effective to prevent the maturation of oocytes. The compounds may be administered on a daily, weekly, or semi-weekly schedule for all or a portion of the menstrual cycle. The compounds may also be formulated for sustained release, e.g., in a monthly implant, semi-yearly implant, and the like.

Methods of Stem Cell Production

Stem cells are primal undifferentiated cells that retain the ability of self-renewal; that is, stem cells are able to divide over several cycles of division and differentiate into other cell types. Stem cells are categorized by their potency, which indicates their ameliorative potential, and their source (e.g., embryonic, adult or cord blood stem cells). Stem cells can be totipotent, pluripotent, multipotent, or unipotent, dependent on the number of different types of cells into which they can differentiate. Stem cells of interest are derived from mammalian sources, e.g. humans and other primates, rates, mice, horses, dogs, cats, etc.

Embryonic stem cells are derived from the undifferentiated inner mass of cells obtained from an early stage embryo (e.g., a blastocyst that is between 50 to 150 cells), which is optionally separated from the other cells of the blastocyst. Embryonic stem cells are usually at least pluripotent in that they have that capability of self renewal (e.g., unlimited expansion) and can differentiate into almost any (if not all) cell type of the organism, including the primary germ layers.

Given the characteristic of self-renewal and their ability to differentiate into almost any cell type, embryonic stem cells are useful in various scientific and medical practices. For instance, embryonic stem cells produced in accordance with the methods of the invention may be used in in vitro differentiation models, e.g., for the study of genes that are involved in the regulation of early development. Additionally, embryonic stem cells produced in accordance with the methods of the invention may be used in the development of regenerative medicine and tissue replacement protocols. Specifically, embryonic stem cells are useful in developing protocols for cell and tissue replacement procedures, for instance, for replacing cells that are damaged through the course of disease, infection, congenital abnormalities and other sources of damage.

Accordingly, in certain embodiments, the invention is directed to the production of embryonic stem cells. Typically the production of an embryonic stem cell involves obtaining and contacting an oocyte with sperm so as to generate an embryo. This may be done as described above, with reference to in vitro fertilization methods, as described below, with reference to somatic cell nuclear transfer methods, by parthenogenetic activation, etc. Alternatively, a preimplantation embryo may be obtained by other means well known in the art.

A collected oocyte is fertilized with a sperm cell or fused with a donor nucleus and activated (as described below). Prior to, during, or following such activation the oocyte or preimplantation cell (e.g., preimplantation embryo) is cultured in a suitable growth culture medium (e.g., a media containing BDNF), which facilitates the development of the resultant cell into a blastocyst but inhibits differentiation. Suitable media that may be combined and act synergistically with BDNF so as to produce a composition of the invention for use in generating and maturing cell colonies (e.g., embryonic cells) are well known in the art and include but are not limited to one or more of: fetal calf serum (FCS), Tissue Culture Medium (TCM), Tyrodes-Albumin-Lactate-Pyruvate (TALP), Dulbecco's Phosphate Buffered Saline (PBS), as well as Eagle's and Whitten's media and the like. The BDNF containing medium may also include serum from one or more additional organisms. Additional media that act synergistically with BDNF are: CR1, which is disclosed in U.S. Pat. No. 5,096,822, and G1.2 and G2.2 media, which are disclosed in Gardner et al., Fertil. Steril. 69:84 (1998); both of which are incorporated herein in their entirety by reference. Any of the above media may be used to culture a fertilized or fused cell of the invention, which may further be co-cultured with a variety of other cell types, such as but not limited to one or more of: fibroblast cells, granulosa cells, oviduct cells, BRL cells, uterine cells, STO cells and the like. Once a blastocyst is formed embryonic stem cells may be isolated and cultured, as described below. Accordingly, in certain embodiments, BDNF is used as a component in culture media to enhance cellular maturation and promote the production of an embryonic stem cell (e.g., at least a pluripotent embryonic stem cell).

Specifically, once the fertilized or fused cell has reached a multicellular stage of development, for instance, the blastocyst stage of development, the blastocyst, and/or isolated inner cell mass (ICM) cells are washed and plated, e.g., on a feeder layer. For example, the blastocyst may be dispersed into a single cell suspension and cultured on a feeder layer of fibroblast cells, such as metabolically inactivated embryonic fibroblast cells, which suspension further includes a BDNF composition of the invention. The feeder cell layer may then secrete soluble factors that promote survival and inhibit differentiation.

Conventionally, the feeder layer of primary embryonic fibroblast is derived from mouse fibroblast (mEF), however, embryonic fibroblast from the same species as the developing blastocyst may be used (as a substitute to mEF) as a feeder layer. In certain embodiments, it may be useful to use human embryonic fibroblast, which may be obtained from several types of sources, as is known in the art, for instance, fibroblast cells derived from human placenta cells. The culture medium of the feeder layer may also contain other suitable factors that are capable inhibiting the differentiation of the cultured cells. After about 9 to 15 days, inner cell mass-derived outgrowths are dissociated into clumps (e.g., of about 50 to 100 cells) which are then replated on fresh embryonic fibroblast containing media. Colonies demonstrating undifferentiated embryonic stem cell morphology are then isolated and replated on fresh embryonic fibroblast media. Embryonic stem cell morphology is characterized as compact colonies with high nucleus to cytoplasm ratio and prominent nucleoli. Embryonic stem cells may thereby be generated. Ideally the embryonic stem cells generated have the following characteristics: they are capable of long-term proliferation in vitro without differentiating, they retain a normal karyotype and they retain the capacity to differentiate into a number of different derivatives, e.g., derivatives from all three embryonic germ layers including endoderm, mesoderm and ectoderm).

Alternatively, the embryonic stem cells may be grown on gelatin plates without fibroblast feeder cells. For instance, embryonic stem cells may be grown on an appropriate substrate (for instance, a substrate including extracellular matrix components) in the presence of a differentiation inhibiting source and/or BDNF medium which has been conditioned by primary fibroblast (e.g., embryonic fibroblast) but is relatively free from feeder cells. For instance, the conditioning process allows an opportunity for the feeder cells to release into the medium soluble factors that replace the role of feeder cells in promoting stem cell survival and growth. BDNF may be added to such a media to further enhance stem cell survival and growth. Accordingly, in certain embodiments, a fibroblast conditioned medium containing BDNF is used in conjunction with a suitable substrate (e.g., MATRIGEL®). For instance, a mouse or human embryonic fibroblast conditioned medium containing BDNF may be used. The culture medium may also contain other suitable factors, such as soluble leukemia inhibitory factor, which replace the activity provided by the feeder cells and are capable of promoting the maturity of the cultured cells but inhibiting their differentiation. Accordingly, BDNF may be used for the production of embryonic stem cells in accordance with both feeder and feeder free culture protocols.

In certain embodiments, it may be desirable to produce embryonic stem cell clones that are genetically identical to a particular organism of interest. For instance, it may be desirable to fuse an oocyte with the genetic material of a donor's somatic cells, e.g., in a somatic cell nuclear transfer protocol. This may be done in accordance with methods well known and practiced in the art, for instance by the protocols set forth in Campbell, K. H. S., McWhir, J., Ritchie, W. A. and Wilmut, A. "Sheep cloned by nuclear transfer from a cultured cell line" (1996) Nature 380 (6569): 64-66 and Wilmut, I., Schnieke, A. E., McWhir, J., Kind, A. J., Campbell, K. H. S. "Viable offspring derived from fetal and adult mammalian cells". (1997) Nature 385 (6619): 810-813; both of which are incorporated herein in their entirety by reference.

Generally, in certain embodiments, one or more unfertilized oocytes is obtained by means well known in the art, such as described above with reference to in vitro fertilization protocols (e.g., via aspiration). In general, as described above, one or more immature oocytes (e.g., a prophase I oocyte) is collected from the ovaries of a donor female. The oocyte is then cultured in a suitable maturation medium (e.g., a BDNF containing medium, as described above) prior to enucleation to promote first polar body extrusion. Once suitably matured, the oocyte may further be cultured in HECM containing hyaluronidase prior to removal of cumulus cells. The one or more oocytes are then screened for polar body extrusion, which indicates the oocyte is at metaphase II. An oocyte arrested at the metaphase II stage can then be activated to accept an introduced nucleus as it would a fertilizing sperm. However, instead of contacting the oocyte with sperm, the nucleus of the oocyte is removed (e.g., the oocyte is enucleated) and the DNA containing nucleus of another cell, for instance, the nucleus of a donor's somatic cell, is transferred into the oocyte. Accordingly, metaphase II oocytes may be placed in HECM (which may contain cytochalasin B), for immediate enucleation, or be placed in a suitable medium, for example an embryo culture medium (such as a medium containing CR1 in addition to BDNF) and then enucleated later.

Enucleation may be effected by methods well known in the art, such as set forth in U.S. Pat. No. 4,994,384 which is incorporated by reference herein. For instance, enucleation may be accomplished microsurgically using a micropipette to remove the polar body and the adjacent cytoplasm and the oocytes may then be screened to identify those of which have been successfully enucleated. The oocytes that have been successfully enucleated can then be placed in a suitable culture medium, e.g., CR1 plus 10% serum, prior to nuclear cell transfer. The nucleus of the donor cell may be from any somatic cell, for instance, a differentiated or non-differentiated cell that is either serum starved or non-serum starved. In certain embodiments, the somatic cell is a cell of the same species as the recipient enucleated oocyte and the nucleus of the somatic cell contains all of the genetic information needed to produce the organism from which the cell was removed.

The transfer of the nucleus into the oocyte may be performed by any means known in the art, e.g., by electro or chemical fusion or injection into the oocyte. See for instance, U.S. Pat. No. 4,997,384 (incorporated herein in its entirety by reference). After the transfer is complete the fused cell is activated (e.g., stimulated in such a manner that it starts to divide). The activation may be by means well known in the art, for instance, by applying a cold, electrical or chemical shock to the fused cell or contacting the cell with known activation agents. Prior to or immediately after activation, the fused cell may be cultured in a BDNF containing media to promote preimplantation maturation. The activation period may be from about 16 to about 52 hours (e.g., post aspiration). Accordingly, as described in greater detail herein below, BDNF is useful by itself and in combination with other factors (e.g., ovarian factors such as EGF and related ligands) in promoting the ability of the oocyte cytoplasm to reprogram substituted nuclei from somatic cells following nuclear replacement and cloning.

Once suitably matured, the fused cell may be transferred into a host organism (e.g., implanted into a recipient uterus) for development into a genetic clone of the somatic cell donor organism, for instance, in accordance with the in vitro fertilization methods described above. Alternatively, the fused cell may be cultured, as described above, in a BDNF containing medium and used for the production of embryonic stem cells that are genetically identical to the somatic cells of the donor organism. These embryonic stem cells may then be processed to generate tissue cells (e.g., organs) that may then be transplanted into a recipient organism. For instance, a donor's own stem cells can be produced and induced to differentiate into cell types of choice and then be transplanted back into the donor for the amelioration of a particular cellular based disease. Typically, because the stem cells (and/or tissues) produced in this manner are genetically compatible with the donor organism the immune system of the donor organism will not reject differentiated cells derived from these stem cells.

Accordingly, BDNF containing compositions of the invention may be used in the generation of a genetic clone (e.g., to enhance preimplantation embryo development) as well as in the creation of stem cells that are genetically compatible with the cells of a donor organism (which may then be used for therapeutic purposes. For instance, embryonic stem cells produced in accordance with the methods of the invention may be useful for the treatment of diabetes, leukemia, heart defects and other congenital diseases.

It is to be noted that although the above has been set forth with respect to the generation of cloned embryonic cells, for instance, by use of somatic cell nuclear transfer protocols, the various methods and steps used for the production of such embryonic cells may vary dependent on the particular protocol used. For instance, BDNF containing compositions of the invention enhance parthenogenetic activation of oocytes and are useful in parthenogenetic activation protocols for the production of embryonic stem cell and/or clones. Methods of parthegenetic activation of human oocytes are known in the art. For example, Balakier et al. (1993) Human Reproduction 8:740-743 describe experimentally induced parthenogenetic activation of human oocytes. Rogers et al. (2004) Reproduction (2004) 128 697-702, describes the induction of parthenogenesis by ubregulation of PLCζ and triggering of $Ca^{++}$ oscillations, Winston et al. (1991) *Fertil Steril.* 1991 November; 56(5):904-12 describe parthenogenetic activation and development of fresh and aged human oocytes using a calcium ionophore.

Modulation of TrkB Activity

In one embodiment of the invention, genetic agents are used to modulate expression of BDNF or TrkB for contraception or enhancement of fertility. The genetic sequences, gene fragments, or antisense sequences are useful in gene therapy. Inhibition can be achieved in a number of ways. Antisense or siRNA sequences may be administered to inhibit expression. Upregulating activity is also of interest, for example through the introduction of mutations that have a gain of function mutation, through increasing expression levels, through administering agents that bind to and activate TrkB, etc.

Expression vectors may be used to introduce the BDNF or TrkB gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day; more usually for a period of at least about several days to several weeks.

The BDNF or TrkB sequence may be introduced into tissues or host cells by any number of routes, including viral infection, microinjection, or fusion of vesicles. Jet injection may also be used for intramuscular administration, as described by Furth et al., (1992) Anal Biochem 205:365-368. The DNA may be coated onto gold microparticles, and delivered intradermally by a particle bombardment device, or "gene gun" as described in the literature (see, for example, Tang et al. (1992) Nature 356:152-154), where gold microprojectiles are coated with the BDNF or TrkB DNA, then bombarded into the cells.

Antisense molecules can be used to down-regulate expression of BDNF or TrkB in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of such molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

In addition to antisense, small interfering RNA (siRNA) duplexes can be used to inhibit expression of jeb genes. siRNA are double stranded RNA molecules of at least about 18 nucleotides, and may be up to the length of the complete mRNA. Preferred siRNA for use in mammalian cells are from about 18 to 30 nucleotides, preferably from about 21 to 22 nucleotides in length. For example, see Elbashir et al., (2001) Nature 411:494-498.

Antisense oligonucleotides may be chemically synthesized by methods known in the art (see Wagner et al., (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars, heterocyclic bases, morpholino derivatives, and the like.

Agents that block BDNF or TrkB activity provide a point of intervention in an important signaling pathway, and are useful as contraceptives. Numerous agents are useful in reducing BDNF or TrkB activity, including agents that directly modulate BDNF or TrkB expression as described above, e.g. expression vectors, anti-sense specific for BDNF or TrkB; and agents that act on the BDNF or TrkB protein, e.g. specific antibodies and analogs thereof, small organic molecules that block activity, etc.

Compound Screening

Compound screening may be performed using an in vitro model, a cell or animal, or purified protein corresponding to BDNF (SEQ ID NO:2) or TrkB (SEQ ID NO:4). One can identify ligands that bind to, inhibit, modulate or mimic the action of the encoded polypeptide. Additionally, screening for BDNF agonists is of particular interest, for example using oocytes expressing TrkB.

Polypeptides useful in screening include those encoded by SEQ ID NO:2 and SEQ ID NO:4, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain and/or a region associated with a consensus sequence). Variants also include fragments of the polypeptides discussed herein, particularly biologically active fragments and/or fragments corresponding to functional domains. Fragments of interest will typically be at least about 10 aa to at least about 15 aa in length, usually at least about 50 aa in length, and can be as long as 100 aa in length or longer, but will usually not exceed about 300 aa in length, where the fragment will have a contiguous stretch of amino acids that is identical to a polypeptide encoded by SEQ ID NO:2 and/or SEQ ID NO:4, or homologs thereof.

Compound screening identifies agents that modulate function of BDNF or TrkB, particularly with respect to their effect on oocyte maturation, development and survival. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. Knowledge of the 3-dimensional structure of the encoded protein, derived from crystallization of purified recombinant protein, could lead to the rational design of small drugs that specifically inhibit activity. These drugs may be directed at specific domains, binding sites, and the like.

The term "agent" as used herein describes any molecule, e.g. protein or pharmaceutical, with the capability of altering, inhibiting, or mimicking the physiological function of BDNF or TrkB. Generally, a plurality of assay mixtures is run in parallel with different agent concentrations to obtain a differential response to the various concentrations. Typically one of these concentrations serves as a negative control, i.e., at zero concentration or below the level of detection.

Candidate agents encompass numerous chemical classes, though typically they are organic molecules, preferably small organic compounds having a molecular weight of more than 50 and less than about 5,000 daltons or less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Libraries of candidate compounds can also be prepared by rational design. (See generally, Cho et al., *Pac. Symp. Biocompat.* 305-16, 1998); Sun et al., *J. Comput. Aided Mol. Des.* 12:597-604, 1998); each incorporated herein by reference in their entirety). For example, libraries of inhibitors can be prepared by syntheses of combinatorial chemical libraries (see generally DeWitt et al., *Proc. Nat. Acad. Sci. USA* 90:6909-13, 1993; International Patent Publication WO 94/08051; Baum, *Chem. & Eng. News,* 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat. Acad. Sci. USA* 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Candidate agents of interest also include peptides and derivatives thereof, e.g., high affinity peptides or peptidomimetic ligands for TrkB, mimetics of BDNF that bind to its receptor but do not activate signaling, agents that block BDNF binding to TrkB, and the like.

Generally, peptide agents encompassed by the methods provided herein range in size from about 3 amino acids to about 100 amino acids, with peptides ranging from about 3 to about 25 being typical and with from about 3 to about 12 being more typical. Peptide agents can be synthesized by standard chemical methods known in the art (see, e.g., Hunkapiller et al., *Nature* 310:105-11, 1984; Stewart and Young, *Solid Phase Peptide Synthesis*, 2nd Ed., Pierce Chemical Co., Rockford, Ill., (1984)), such as, for example, an automated peptide synthesizer. In addition, such peptides can be produced by translation from a vector having a nucleic acid sequence encoding the peptide using methods known in the art (see, e.g., Sambrook et al., *Molecular Cloning, A Laboratory Manual*, 3rd ed., Cold Spring Harbor Publish., Cold Spring Harbor, N.Y. (2001); Ausubel et al., *Current Protocols in Molecular Biology*, 4th ed., John Wiley and Sons, New York (1999); which are incorporated by reference herein).

Peptide libraries can be constructed from natural or synthetic amino acids. For example, a population of synthetic peptides representing all possible amino acid sequences of length N (where N is a positive integer), or a subset of all possible sequences, can comprise the peptide library. Such peptides can be synthesized by standard chemical methods known in the art (see, e.g., Hunkapiller et al., *Nature* 310:105-11, 1984; Stewart and Young, *Solid Phase Peptide Synthesis*, $2^{nd}$ Ed., Pierce Chemical Co., Rockford, Ill., (1984)), such as, for example, an automated peptide synthesizer. Nonclassical amino acids or chemical amino acid analogs can be used in substitution of or in addition into the classical amino acids. Non-classical amino acids include but are not limited to the D-isomers of the common amino acids, α-amino isobutyric acid, 4-aminobutyric acid, 2-amino butyric acid, γ-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hour will be sufficient.

Preliminary screens can be conducted by screening for compounds capable of binding to BDNF or TrkB, as at least some of the compounds so identified are likely BDNF or TrkB inhibitors. The binding assays usually involve contacting BDNF or TrkB with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. The BDNF or TrkB protein utilized in such assays can be naturally expressed, cloned or synthesized.

Certain screening methods involve screening for a compound that modulates the expression of BDNF or TrkB. Such methods generally involve conducting cell-based assays in which test compounds are contacted with one or more cells expressing BDNF or TrkB and then detecting and an increase in expression (either transcript or translation product). Some assays are performed with oocyte cells that express endogenous TrkB, or follicular cells that express BDNF.

BDNF or TrkB gene expression can be detected in a number of different ways. The expression level of BDNF or TrkB in a cell can be determined by probing the mRNA expressed in a cell with a probe that specifically hybridizes with a probe or transcript. Probing can be conducted by lysing the cells and conducting Northern blots or without lysing the cells using in situ-hybridization techniques. Alternatively, BDNF or TrkB protein can be detected using immunological methods in which a cell lysate is probe with antibodies that specifically bind to BDNF or TrkB.

Other cell-based assays are reporter assays conducted with cells that do not express BDNF or TrkB. Certain of these assays are conducted with a heterologous nucleic acid construct that includes a BDNF or TrkB promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase; Alton and Vapnek (1979) Nature 282:864-869), luciferase, β-galactosidase and alkaline phosphatase (Toh, et al. (1980) Eur. J. Biochem. 182:231-238; and Hall et al. (1983) J. Mol. Appl. Gen. 2:101).

In these assays, cells harboring the reporter construct are contacted with a test compound. A test compound that either activates the promoter by binding to it or triggers a cascade that produces a molecule that activates the promoter causes expression of the detectable reporter. Certain other reporter assays are conducted with cells that harbor a heterologous construct that includes a transcriptional control element that activates expression BDNF or TrkB and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

The level of expression or activity can be compared to a baseline value. The baseline value can be a value for a control sample or a statistical value that is representative of BDNF or TrkB expression levels for a control population. Expression levels can also be determined for cells that do not express BDNF or TrkB as a negative control. Such cells generally are otherwise substantially genetically the same as the test cells.

Various controls can be conducted to ensure that an observed activity is authentic including running parallel reactions with cells that lack the reporter construct or by not contacting a cell harboring the reporter construct with test compound. Compounds can also be further validated as described below.

Active test agents identified by the screening methods described herein that modulate BDNF or TrkB activity can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Once analogs have been prepared, they can be screened using the methods disclosed herein to identify those analogs that exhibit an increased ability to modulate BDNF or TrkB activity, for example in an in vitro assay involving maturation of oocytes. Such compounds can then be subjected to further analysis to identify those compounds that appear to have the greatest potential as pharmaceutical agents. Alternatively, analogs shown to have activity through the screening methods can serve as lead compounds in the preparation of still further analogs, which can be screened by the methods described herein. The cycle of screening, synthesizing analogs and re-screening can be repeated multiple times.

Antibodies Specific for BDNF or TrkB Polypeptides

Antibodies specific for BDNF or TrkB or epitopic fragments thereof may be used in the methods of the invention as agonists or antagonists. Agonists will typically bind to and activate the TrkB receptor, while antagonists will block the interaction between BDNF and TrkB. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for an BDNF or TrkB polypeptide.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

Compositions

Compounds identified by the screening methods described above, including BDNF and analogs thereof, can serve as the active ingredient in pharmaceutical compositions formulated for use in the improvement of fertility, in vivo, or as media components for use in in vitro fertilization and stem cell production protocols, as described above. BDNF, its mimetics and analogs or derivatives thereof may be used in compositions of the invention either alone or in combination with other agents.

Other agents that may be included in a composition of the invention comprise any agent that can enhance the maturation and/or promote (and thereby act synergistically with BDNF) the growth and development of an oocyte, zygote or embryo either in vivo or in vitro. For instance, suitable agents may be those that promote cell growth, proliferation and differentiation. Specifically, suitable agents that may be incorporated into a composition of the invention, which act synergistically with BDNF, include but are not limited to one or more of the other neurotrophins (including: NGF, NTF3 and NTF4/5), growth factors, epidermal growth factor (EGF), EGF-like factors (e.g., factors that stimulate the EGFR receptor), heparin-binding growth factor (e.g., midkine), meiosis-activating sterol factors (e.g., activin), TGFα, insulin-like 3, or the like. Other agents that act synergistically with BDNF and may be included as a component in a composition in combination with BDNF include gonadotropin releasing hormone (GnRH), follicle stimulating hormone (FSH), antagonist of inhibin (e.g., inhibin B), luteinizing hormone (LH), TSH, hCG, androgens, estrogens, progesterone, other maturation-promoting factors and the like.

Antagonists to BDNF, e.g., competitive inhibitors (such as k252a, corticosterone, and the like) can also be used in compositions and used as a contraceptive.

These compositions can include various other agents to enhance delivery and efficacy as well as agents to enhance delivery and stability of the active ingredients. For example, the compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The compositions may also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient (e.g., BDNF), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which consist of the packaged active ingredient with a suppository base. Suitable suppository bases include natural or synthetic triglycerides or paraffin hydrocarbons. In addition, it is also possible to use gelatin rectal capsules, which consist of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the targeted site, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 μg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Induction of Oocyte Maturation and Development

Optimal development of fertilized eggs into preimplantation embryos is essential for reproduction. Because LH interacts only with ovarian somatic cells, its potential regulation of oocyte function is may be mediated by local paracrine factors. Herein described are DNA microarray analyses of ovarian transcripts. Brain-derived neurotrophic factor (BDNF) was identified as being secreted by granulosa and cumulus cells and was found to be an ovarian factor stimulated by the preovulatory LH surge. Ovarian BDNF is shown herein to act on TrkB receptors expressed exclusively in oocytes so as to enhance the first polar body extrusion of oocytes and to promote the in vitro development of zygotes into preimplantation embryos.

Furthermore, presented herein below, in vivo treatment with a Trk receptor inhibitor suppressed first polar body extrusion and prevented the progression of zygotes into blastocysts. Thus, ovarian BDNF is determined to be a factor important to nuclear and cytoplasmic maturation of the oocyte, as well as found to be significant for successful oocyte development into preimplantation embryos. Treatment with BDNF therefore is useful for enhancing and inhibiting fertilization as well as for the conditioning of cultured oocytes for optimal progression into totipotent blastocysts, e.g., for the production of stem cells.

In vertebrates, rupture of ovarian follicles and final maturation of oocytes occur in response to stimulation by pituitary-derived luteinizing hormones (LH) that act on the somatic granulosa and theca cells surrounding the oocyte. Shortly after stimulation by the preovulatory surge of LH, oocytes arrested at the late prophase stage resume meiosis characterized by germinal vesicle (nuclear envelope) breakdown (GVBD), chromosome condensation, and extrusion of the first polar body in preparation for fertilization and early embryonic development. The endocrine hormone LH stimulates ovarian production of EGF-like factors from granulosa cells and insulin-like 3 from theca cells to promote GVBD.

Brain-derived neurotrophic factor (BDNF) plays an important role in the ovaries, where it is important for the development of early follicles as well as for oocyte maturation and preimplantation embryo development. As set forth below, major increases in BDNF expression after LH/human chorionic gonadotropin (hCG) stimulation was observed in both ovarian granulosa and cumulus cells. Additionally, the exclusive expression of the BDNF receptor, TrkB, in oocytes was demonstrated. As shown below, treatment of cultured oocytes with BDNF enhanced first polar body extrusion and increased the competence of oocytes to complete preimplantation development.

Methods:

Animals. Immature female B6D2F1 mice were obtained from Charles River Laboratories. Animal care was consistent with institutional and National Institute of Health guidelines. Mice at 22 days of age were treated with 7.5 units of pregnant mare serum gonadotropin (PMSG; Calbiochem), followed by treatment with 10 units of hCG (Sigma) 48 h later so as to simulate follicle maturation and ovulation.

DNA Microarray Analyses. Mice (n=108) were injected at 21 days of age with Humegon (7.5 units per animal, Organon)

containing follicle-stimulating hormone and LH in order to stimulate follicular growth. Forty-eight hours later, some animals were treated i.p. with Pregnyl (5 units per animal) containing LH activity to induce ovulation. Ovaries were dissected from animals killed bi-hourly after Humegon treatment (three mice per group) and hourly after Pregnyl treatment (one mouse per group) for RNA extraction (TRIzol, Invitrogen). Aliquots of 6 µg of total RNA at 1 µg/µl for one-chipset hybridization were stored at −80° C. Samples were hybridized to the Affymetrix mouse MGU74v2 arrays A, B, and C according to standard Affymetrix protocols. The pooled follicular phase samples were hybridized in duplicate, and the postPregnyl samples were single determinations.

Follicle Cultures. Preovulatory follicles were excised from mouse ovaries 48 h after PMSG treatment and cultured to examine nuclear maturation of oocytes (Kawamura et al. (2004) Proc. Natl. Acad. Sci. USA 101, 7323-7328). Follicles (20-30 per vial) were cultured with or without recombinant human BDNF (Pepro-Tech, Rocky Hill, N.J.) or 5 µg/ml LH (Organon) in Leibovitz's L-15 medium (Invitrogen). The vials were flushed at the start of the culture with $O_2/N_2$ (at a 1:1 ratio), sealed, and cultured at 37° C. with gentle shaking for 6 h. After culture, cumulus oocyte complexes (COCs) were isolated, and, after cumulus cells were removed, oocytes were examined for the occurrence of GVBD.

Evaluation of First Polar Body Extrusion. For evaluating the transition from metaphase I stage to metaphase II (MII) stage oocytes, COCs were obtained from mouse ovaries 48 h after PMSG treatment by puncturing the largest follicles in M2 medium (Specialty Media, Phillipsburg, N.J.). COCs were washed twice, transferred to modified M16 medium (Specialty Media) without FBS, and cultured with or without different doses of BDNF, mouse nerve growth factor (NGF; R & D Systems), or human neurotrophin-3 (NT-3) (R & D Systems) for 20 h at 37° C. in 5% $CO_2$/95% air. Some COCs were also cultured with BDNF with or without the TrkB ectodomain (R & D Systems), pan-specific Trk receptor inhibitor K252a (Calbiochem), or K252b. The occurrence of first polar body extrusion in the oocyte was examined after removing cumulus cells by using a small-bore pipette under Hoffman contrast microscopy (Nikon).

In Vitro Maturation, Fertilization, and Early Embryonic Development. We performed in vitro maturation of oocytes followed by in vitro fertilization as previously described, with slight modifications. COCs from PMSG-primed mice were obtained in the M2 medium supplemented with 5% FBS before culturing in minimum essential media-α (Invitrogen) supplemented with Earle's salts, 10 µg/ml streptomycin sulfate, 75 µg/ml penicillin G, and 5% FBS in the presence or absence of 3 ng/ml BDNF at 37° C. in 5% $CO_2$/95% air. After 16 h of treatment, cumulus cells were removed and the oocytes were examined and classified according to their developmental stage (germinal vesicle, metaphase I, or MII). MII-stage oocytes were inseminated with sperm from B6D2F1 males and incubated for 4 h at 37° C. in 5% $CO_2$/95% air. After in vitro fertilization, fertilized oocytes were recovered, washed three times, and cultured in human tubal fluid medium (Specialty Media). The following morning, two-cell stage embryos were collected and cultured in 2 ml of modified M16 medium for 5 days more up to the blastocyst stage at 37° C. in 5% $CO_2$/95% air. Embryonic development was monitored daily by Hoffman modulation contrast microscopy, and the progression of fertilized eggs to preimplantation embryos was assessed.

In Vivo Analysis. To evaluate first polar body extrusion, immature mice were treated with 7.5 units of PMSG followed by 10 units of hCG 48 h later with or without an i.p. injection of K252a (dissolved in 10% dimethyl sulfoxide/0.9% saline). For negative controls, the plasma membrane nonsoluble K252b was used. Twelve hours after hCG injection, ovulated COCs were obtained from the oviducts. After treatment with hyaluronidase (Specialty Media) for 1-2 min, oocytes were separated from cumulus cells and the proportion of oocytes showing first polar body extrusion was evaluated. To evaluate the role of BDNF in the conditioning of oocytes for early embryo development, immature mice were treated with PMSG, followed by hCG as described above. Immediately after hCG injection, animals were allowed to mate before collection of fertilized oocytes 22 h later. To ensure the suppression of Trk receptor activity, 10 µg of K252a or K252b was administrated i.p. at 0, 4, and 8 h after hCG injection. Fertilized oocytes were separated from cumulus cells, washed three times in M2 medium, and cultured for 5 days in modified M16 medium. Embryonic development was monitored daily, and the progression of fertilized eggs into preimplantation embryos was assessed.

Figure 1D:
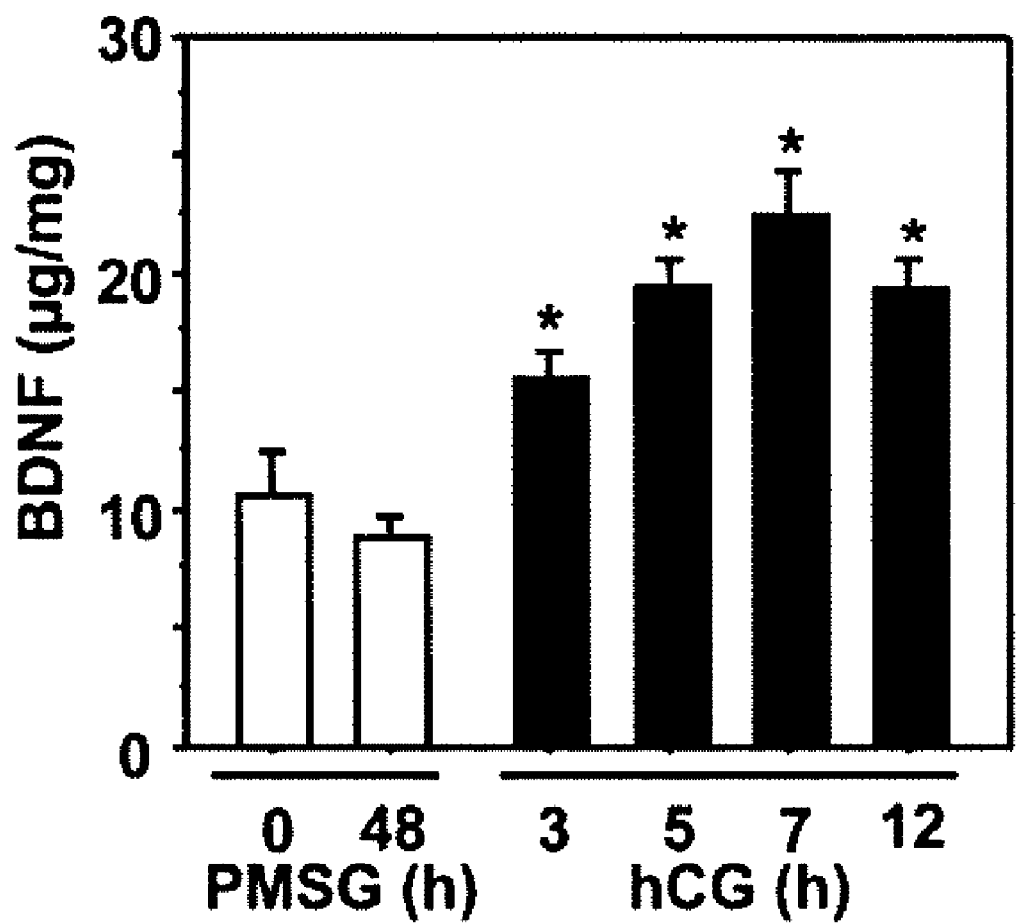

Accordingly, in accordance with the above methods, DNA microarray analyses were employed to identify ovarian paracrine ligands induced by LH during the preovulatory period. Immature mice were treated with Humegon (containing follicle-stimulating hormone and LH activities) and Pregnyl (containing LH/hCG activity) to stimulate follicular maturation and ovulation, respectively. As shown in FIG. 1A (line graph), the expression of BDNF mRNA was stimulated after treatment with Humegon or Pregnyl. In contrast, transcript levels for the TrkB receptor and neurotrophin-4/5 (NT-4/5) showed minor changes (FIGS. 1B and C, line graphs). To confirm DNA microarray results, real-time RT-PCR of ovarian transcripts for these genes was performed in mice treated with PMSG, followed by an injection of an ovulatory dose of hCG 48 h later. In addition to demonstrating preovulatory increases in BDNF transcripts (FIG. 1, bar graph), the stimulatory effect of hCG/Pregnyl on ovarian BDNF proteins was detected by using ELISA (FIG. 1D). Treatment with hCG increased ovarian BDNF antigen levels within 3 h, followed by a peak at 7 h.

Figure 2A:
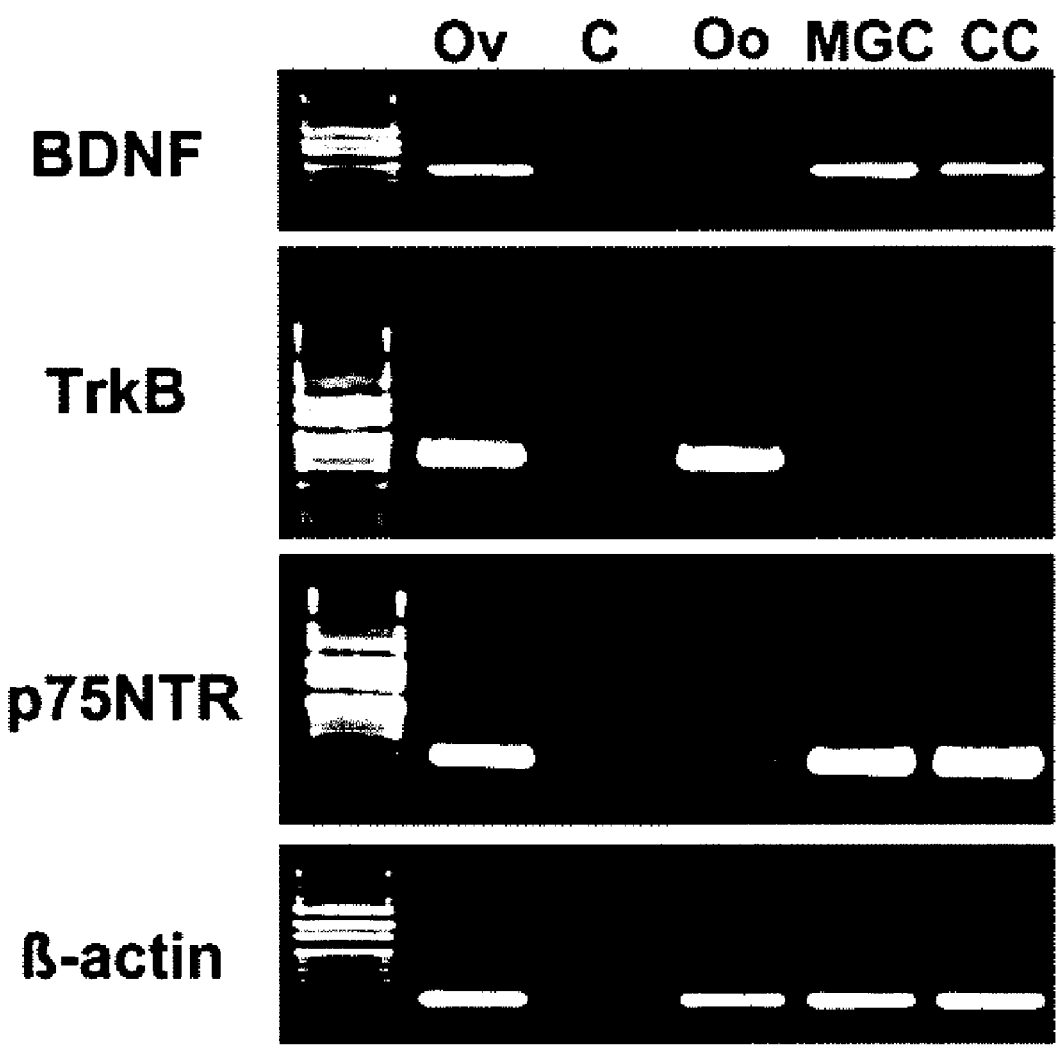

By using isolated ovarian cells, RT-PCR was performed to examine cells expressing BDNF and TrkB in the mouse ovary. The expression of the low-affinity receptor p75NTR for neurotrophins was also examined. Expression of the BDNF transcript was detected in mural granulosa and cumulus cells but not in oocytes from mice primed with PMSG for 48 h (FIG. 2A). In contrast, TrkB mRNA was expressed exclusively in oocytes, although the p75 NTR transcript was found in granulosa cells, oocytes (FIG. 2A), and the theca shell. The localization of BDNF and TrkB proteins was also confirmed by using immunohistochemistry.

Figure 2C:
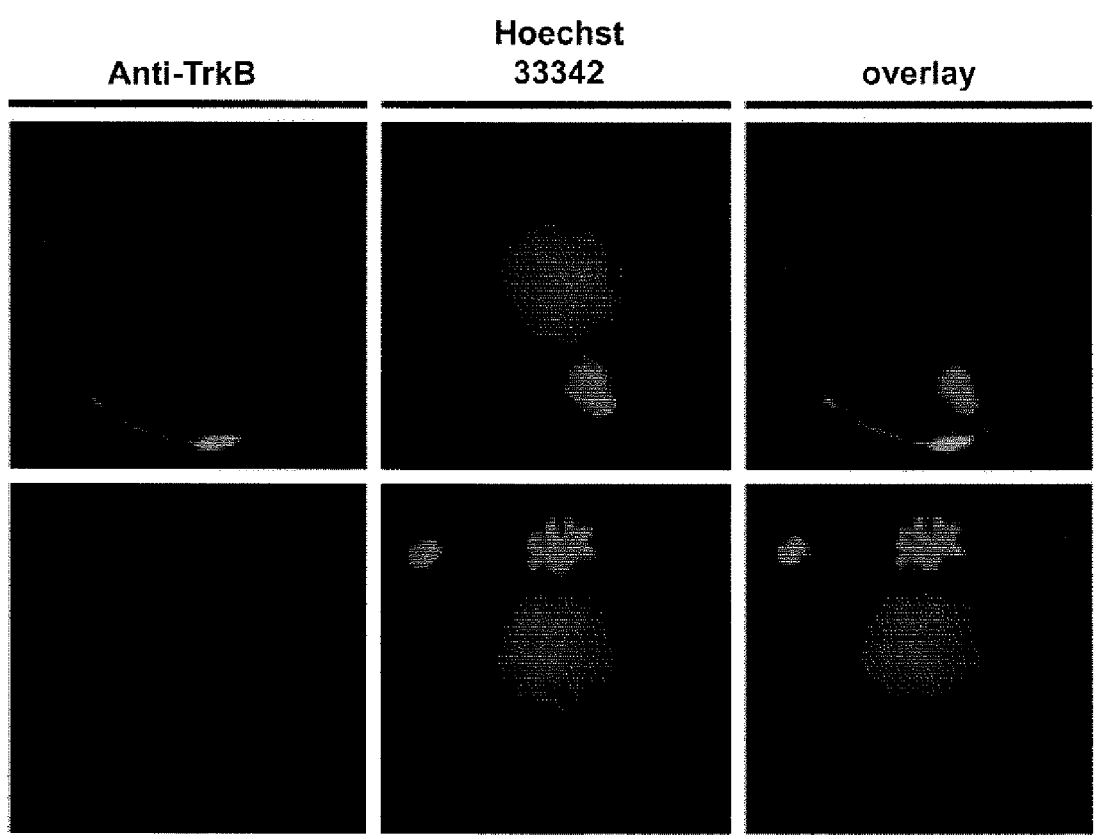

As shown in FIG. 2B and FIG. 5, strong BDNF staining was observed in mural and cumulus granulosa cells of preovulatory follicles at 7 h after hCG treatment, and a weaker signal was found in mural granulosa cells in small antral follicles. In addition, TrkB expression in the plasma membrane of the oocyte was confirmed by using immunofluorescence staining (FIG. 2C).

Based on hCG stimulation of BDNF expression in ovarian somatic cells and the exclusive expression of TrkB in oocytes, BDNF is shown to act as a paracrine factor to regulate oocyte function. In cultured preovulatory follicles, treatment with LH, but not BDNF, for 6 h induced GVBD in oocytes (FIG. 3A). Furthermore, treatment with BDNF, unlike LH, did not induce cumulus cell expansion. Because oocytes obtained from preovulatory follicles underwent spontaneous GVBD when cultured as cumulus oocyte complexes (COC), the COC model was used to test the effect of BDNF to promote further oocyte development. As shown in FIG. 3B, treatment with BDNF, but not the related NGF or NT-3, increased first polar body extrusion in cultured oocytes in a dose-dependent manner. In addition, the stimulatory effect of BDNF was blocked by cotreatment with the TrkB ectodomain (FIG. 3C), whereas treatment with the TrkB ectodomain alone was ineffective. The Trk receptor inhibitor K252a was also used to block TrkB function in the oocyte.

As shown in FIG. 3C, concomitant treatment with K252a, but not the membrane nonsoluble K252b, suppressed the stimulatory effect of BDNF on first polar body extrusion. Because BDNF, but not related neurotrophins, are increased during the preovulatory period, K252a was further used to examine the role of endogenous BDNF on oocyte function in vivo. Although treatment with K252a or K252b did not affect the number of ovulated oocytes per animal (vehicle, 40.2±7.5; K252a-treated, 37.8±5.3; K252b-treated, 38.4±8.7), treatment with K252a inhibited by 30% the first polar body extrusion by ovulated oocytes (FIG. 3D). In contrast, similar treatment with K252b was ineffective. Of interest, >95% of ovulated oocytes from all groups showed GVBD accompanied by expansion of the cumulus cells.

The role of BDNF in conditioning the oocytes for subsequent fertilization and progression to blastocysts was evaluated in vitro (FIG. 4). COCs obtained from mice primed for 48 h with PMSG were cultured and treated with or without BDNF. To avoid hardening of the zona pellucida that is unfavorable for in vitro fertilization, 5% FBS was included for all cultures. Similar to serum-free cultures (FIG. 3B), treatment with BDNF increased more than 2-fold the proportion of oocytes showing first polar body extrusion (FIG. 4A, MII-stage oocytes). These MII oocytes were then fertilized in vitro without further treatment with BDNF. As shown in FIG. 4A, pretreatment with BDNF increased by 2- and 5-fold the proportions of MII oocytes that developed into the two-cell and blastocyst-stage embryos, respectively.

Because the oocyte content of glutathione is important to sperm nuclear decondensation, the glutathione concentration in oocytes also was evaluated. As shown in FIG. 4B, glutathione levels were low in germinal vesicle-stage oocytes and in oocytes that spontaneously completed first polar body extrusion in vitro. However, treatment with BDNF increased glutathione content in MII oocytes (FIG. 4B).

By using a Trk receptor inhibitor, the role of endogenous BDNF in conditioning the preovulatory oocytes for optimal development into preimplantation embryos was further examined. PMSG-primed animals were treated with hCG with or without K252a and mated with fertile males. Twenty-two hours after hCG treatment, fertilized oocytes were obtained from the oviduct and cultured in vitro. Although the number of fertilized oocytes did not differ between the control and K252a-treated groups, treatment with K252a suppressed by 72% the development of zygotes into blastocyst stage embryos (FIG. 4C). In contrast, treatment with K252b was ineffective. Because many blastocysts are smaller in the K252a-treated group (FIG. 4E), the number of cells in the blastocysts were counted and found to be decreased by 51% after K252a, but not K252b, treatment (FIG. 4D).

As can be seen with reference to FIG. 4 deficient or defective cytoplasmic maturation of the oocyte is indicative of oocytes being incompetent to complete nuclear maturation and therefore unable to develop into the blastocyst stage. During maturation of preovulatory oocytes, cytoplasmic changes in oocytes are necessary to allow for the acquisition of the maternal components required for optimal development of fertilized oocytes into preimplantation embryos. Accordingly, as shown herein, the in vitro treatment of COCs with BDNF not only augments first polar body extrusion but also enhances the subsequent development of MII oocytes to two-cell and blastocyst embryos. Further, in vivo treatment with the Trk receptor inhibitor demonstrates a major suppression of embryos capable of developing into the blastocyst stage. Even for embryos developed to the blastocyst stage, pretreatment with the Trk receptor inhibitor decreased their cell numbers by half. Furthermore, oocytes that spontaneously reach the first polar body stage have lower levels of glutathione (FIG. 4B), which is important in the fertilization of MII oocytes by facilitating sperm nuclear decondensing activity.

Accordingly, the above results demonstrate the essential role of BDNF as an ovarian paracrine factor that promotes first polar body extrusion and as a conditioning agent that prepares post ovulation oocytes for optimal fertilization and development into preimplantation embryos. Additionally, because BDNF treatment enhances oocyte glutathione content, BDNF plays a key role in successful fertilization. Thus, ovarian BDNF activates downstream pathways in the oocyte to facilitate nuclear maturation (first polar body extrusion) as well as fertilization (glutathione content) and early embryo development. Hence, the inhibition of BDNF activity can be used as an effective method of contraception. The in vitro and in vivo results above demonstrate that BDNF is essential for first polar body extrusion as well as for cytoplasmic maturation of the oocyte, which is important for early embryo development.

All publications and patent applications cited in this specification are herein incorporated by reference as if each individual publication or patent application were specifically and individually indicated to be incorporated by reference. The publications discussed herein are provided solely for their disclosure prior to the filing date of the present application. Nothing herein is to be construed as an admission that the invention is not entitled to antedate such a disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of enhancing fertility, the method comprising contacting a mammalian oocyte in vitro with BDNF or an agonist thereof in a dose effective to promote cytoplasmic changes essential for monospermic fertilization and processing of the sperm.

2. The method of claim 1, wherein said contacting includes contacting said oocyte when said oocyte is cultured.

3. The method of claim 1, further comprising the step of fertilizing said oocyte with a sperm.

4. The method of claim 1, wherein said oocyte is a nonhuman mammalian oocyte and further comprising the steps of: enucleating said nonhuman mammalian oocyte; and transplanting a nonhuman mammalian nucleus into the enucleated oocyte.

5. The method of claim 1, further comprising the step of parthenogenetic activation of said oocyte.

6. A method of enhancing in vitro fertilization, the method comprising contacting a mammalian oocyte in vitro with BDNF, or an agonist thereof in a dose effective to promote cytoplasmic changes essential for monospermic fertilization, processing of the sperm, and pre-implantation embryo development; and implanting said oocyte into the uterus of a host organism.

7. The method of claim 6, wherein said contacting includes contacting said oocyte when said oocyte is cultured.

8. A method of enhancing fertility, the method comprising contacting a mammalian embryo in vitro with BDNF or an agonist thereof in a dose effective to promote cytoplasmic changes essential for pre-implantation embryo development.

9. A method of enhancing in vitro fertilization, the method comprising contacting an mammalian embryo in vitro with BDNF, or an agonist thereof in a dose effective to promote cytoplasmic changes essential for pre-implantation embryo development; and implanting said embryo into the uterus of a host mammal.

* * * * *

UNITED STATES PATENT AND TRADEMARK OFFICE
CERTIFICATE OF CORRECTION

| | | |
|---|---|---|
| PATENT NO. | : 7,763,462 B2 | Page 1 of 1 |
| APPLICATION NO. | : 11/762606 | |
| DATED | : July 27, 2010 | |
| INVENTOR(S) | : Kazuhiro Kawamura | |

It is certified that error appears in the above-identified patent and that said Letters Patent is hereby corrected as shown below:

In column 1 lines 15-17: Please delete the paragraph starting with "This invention" ending with "in this invention." and replace with the following paragraph:

--This invention was made with Government support under contract HD031398 awarded by the National Institutes of Health. The Government has certain rights in this invention.--

Signed and Sealed this
Second Day of October, 2012

David J. Kappos
*Director of the United States Patent and Trademark Office*